United States Patent
Thompson et al.

(10) Patent No.: US 11,024,403 B2
(45) Date of Patent: Jun. 1, 2021

(54) METHOD FOR ANALYZING AND OPTIMIZING METABOLIC NETWORKS

(71) Applicant: X Development LLC, Mountain View, CA (US)

(72) Inventors: Jason Thompson, Redwood City, CA (US); Frank Russo, Sunnyvale, CA (US)

(73) Assignee: X DEVELOPMENT LLC, Mountain View, CA (US)

(*) Notice: Subject to any disclaimer, the term of this patent is extended or adjusted under 35 U.S.C. 154(b) by 724 days.

(21) Appl. No.: 15/876,962

(22) Filed: Jan. 22, 2018

(65) Prior Publication Data

US 2019/0228130 A1    Jul. 25, 2019

(51) Int. Cl.
| | | |
|---|---|---|
| *G01N 33/48* | (2006.01) | |
| *G01N 33/50* | (2006.01) | |
| *G16B 5/00* | (2019.01) | |
| *G16C 20/10* | (2019.01) | |
| *G06F 16/332* | (2019.01) | |
| *G06F 16/901* | (2019.01) | |

(52) U.S. Cl.
CPC ............ *G16B 5/00* (2019.02); *G06F 16/3328* (2019.01); *G06F 16/9024* (2019.01); *G16C 20/10* (2019.02)

(58) Field of Classification Search
CPC ....... G16B 5/00; G16C 20/10; G06F 16/3328; G06F 16/9024
See application file for complete search history.

(56) References Cited

FOREIGN PATENT DOCUMENTS

WO    WO 2014/015196 A2    1/2014

OTHER PUBLICATIONS

Hatzimanikatis et al. Analysis and design of metabolic reaction networks via mixed-integer linear optimization. AIChE Journal, vol. 42, pp. 1277-1292. (Year: 1996).*
International Search Report and Written Opinion issued in Application No. PCT/US2018/066036 dated Apr. 12, 2019.
Balaji Veeramani et al., "Predicting functional associations from metabolism using bi-partite network algorithms", BMC Systems Biology, 2010, 4:95, pp. 1-15.
Sudhakar Jonnalagadda et al., "An efficient graph theory based method to identify every minimal reaction set in a metabolic network", BMC Systems Biology, 2014, 8:28, pp. 1-13.
(Continued)

*Primary Examiner* — Russell S Negin
(74) *Attorney, Agent, or Firm* — Kilpatrick Townsend & Stockton LLP

(57) ABSTRACT

A method for analyzing a bipartite graph data structure to condense reaction pathways of a metabolic network is described herein. A cell's metabolic network is structured as a bipartite graph, with molecule nodes representing the molecules within metabolism and edges connecting molecule nodes representing chemical reactions or processes. Molecule nodes within the bipartite graph are categorized according to the number of edges leading into and out of each node. If the structure of the bipartite graph indicates that the molecule node does not contribute to flux value solutions of a mathematical model of the metabolic network, then the node and its connected reaction pathway is blocked or removed from the bipartite graph. Thus the complexity of the bipartite graph may be reduced, and crucial nodes and pathways identified.

20 Claims, 11 Drawing Sheets

(56) References Cited

OTHER PUBLICATIONS

Patrick B Warren et al., "Flux networks in metabolic graphs", Phisical Biology, vol. 6, No. 4, Sep. 2009, pp. 1-9.
International Report on Patentability dated Aug. 6, 2020 in related application No. PCT/US2018/066036, all pgs.

* cited by examiner

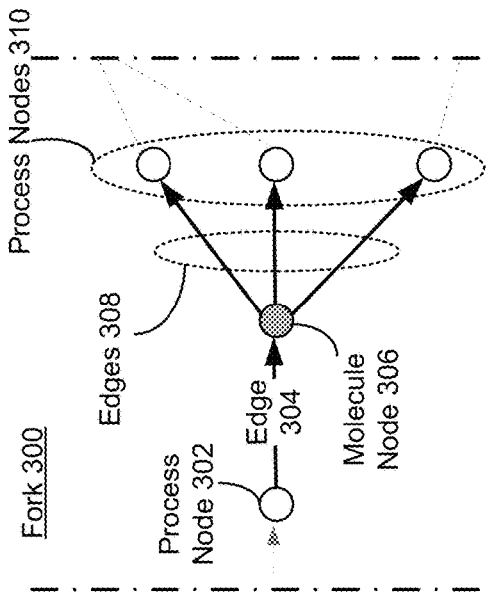
FIG. 3
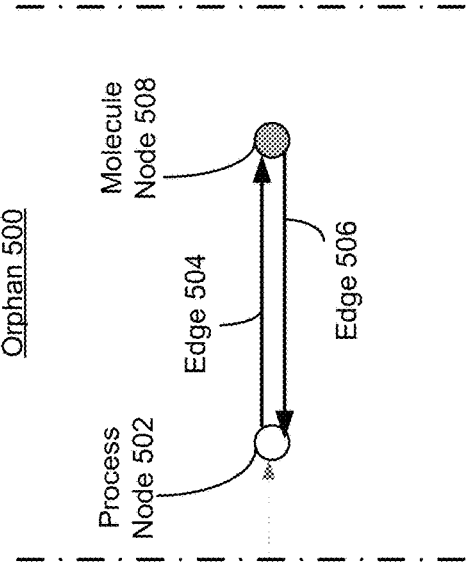
FIG. 5
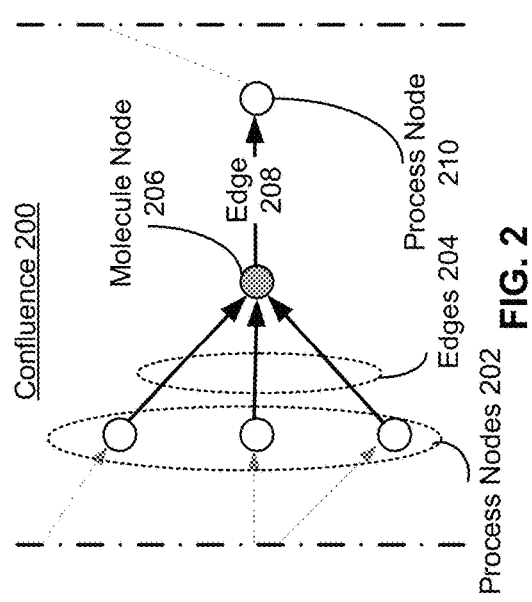
FIG. 2
FIG. 4

1200

1202 — Receiving a metabolic network in a bipartite graph data structure

1204 — Blocking each reaction pathway containing at least one unused or unmade molecule node 1206 — Condensing each reaction pathway containing at least one intermediate molecule node

FIG. 12

METHOD FOR ANALYZING AND OPTIMIZING METABOLIC NETWORKS

BACKGROUND

Field of Art

This description generally relates to identifying characteristics of a metabolic network by analyzing a data structure representation of the network and blocking or removing non-contributing reaction pathways to flux value solutions of the network under steady state assumptions.

Description of the Related Art

The metabolic system of a cell of a living organism can be conceptualized as a linked network of pathways between reactants and products. This linked network can be used in mathematical simulations of metabolism to recreate cellular behavior and attempt to identify crucial metabolic pathways and the effect of changes to metabolism on the larger cellular environment. However, even for simple organisms, the number of molecules and reactions in a metabolic system can range from high hundreds to low thousands. The sheer size of a metabolic network can make it computationally unwieldy, requiring long run-times for each mathematical simulation. Furthermore, because the pathways of the network are often pulled from a variety of sources, such as primary literature, databases and biochemistry texts, it is difficult to assess the correctness of the network with more than a few tens of compounds. The unwieldy nature of the network also makes it difficult to identify crucial pathways in the network, or potential targets for disrupting or influencing metabolism.

SUMMARY

A metabolic network can be structured as a bipartite graph with two distinct sets of nodes. The first are molecule nodes representing molecules within metabolism, and the second are process nodes representing biochemical processes or reactions that may involve multiple molecules in distinct roles. Edges in the bipartite graph connect molecule nodes to the process nodes representing the reactions in which they participate. Edges store information about the role the molecule node plays in the reaction of the process node. By analyzing the structure of the bipartite graph, molecule nodes can be categorized according to the number of edges that lead into and out of each molecule node, where the total number of edges indicates the total number of reactions the molecule has a role in. When the bipartite graph is used in a mathematical simulation of metabolism that makes steady state assumptions, only certain portions of the metabolic network may contribute to the mathematical solutions that result. The steady state assumption provides a set of criteria which may be used to reduce the size of the bipartite graph. Following these criteria and using the edge counts of the nodes allow for the metabolic network to be reduced, thus reducing the computation associated with simulating metabolism and also identifying crucial reaction pathways and molecule nodes to metabolism.

A method for analyzing a bipartite graph data structure to condense reaction pathways of a metabolic network includes receiving a metabolic network in a bipartite graph data structure. The bipartite graph data structure includes a plurality of molecule nodes, and each molecule node is a molecule in a metabolic reaction. The bipartite graph data structure includes a plurality of edges connecting at least two of the plurality of molecule nodes, where each edge leading out of a first molecule node and into a second molecule node represents a metabolic reaction in which the first molecule is a reactant and the second molecule is a product. The method includes determining for each molecule node in the bipartite graph data structure a first number of metabolic reactions for which each molecule is a product based on a first number of edges leading into each molecule node. The method includes determining for each molecule node in the bipartite graph data structure a second number of metabolic reactions for which each molecule is a reactant based on a second number of edges leading out of each molecule node. The method includes, responsive to determining that none of the first number of edges leads into a third molecule node, or none of the second number of edges leads out of the third molecule node, blocking a first reaction pathway of all molecule nodes and edges connecting to the third molecule node in the bipartite graph data structure.

BRIEF DESCRIPTION OF DRAWINGS

FIG. 2 is an illustration of a confluence node in a metabolic network, according to one embodiment.

FIG. 3 is an illustration of a fork node in a metabolic network, according to one embodiment.

FIG. 4 is an illustration of a nexus node in a metabolic network, according to one embodiment.

FIG. 5 is an illustration of an orphan node in a metabolic network, according to one embodiment.

FIG. 12 shows a process for identifying and condensing reaction pathways of a metabolic network with non-zero flux solutions using a structure of a bipartite graph, according to one embodiment.

DETAILED DESCRIPTION OF DRAWINGS

I. Context

Figure 1:
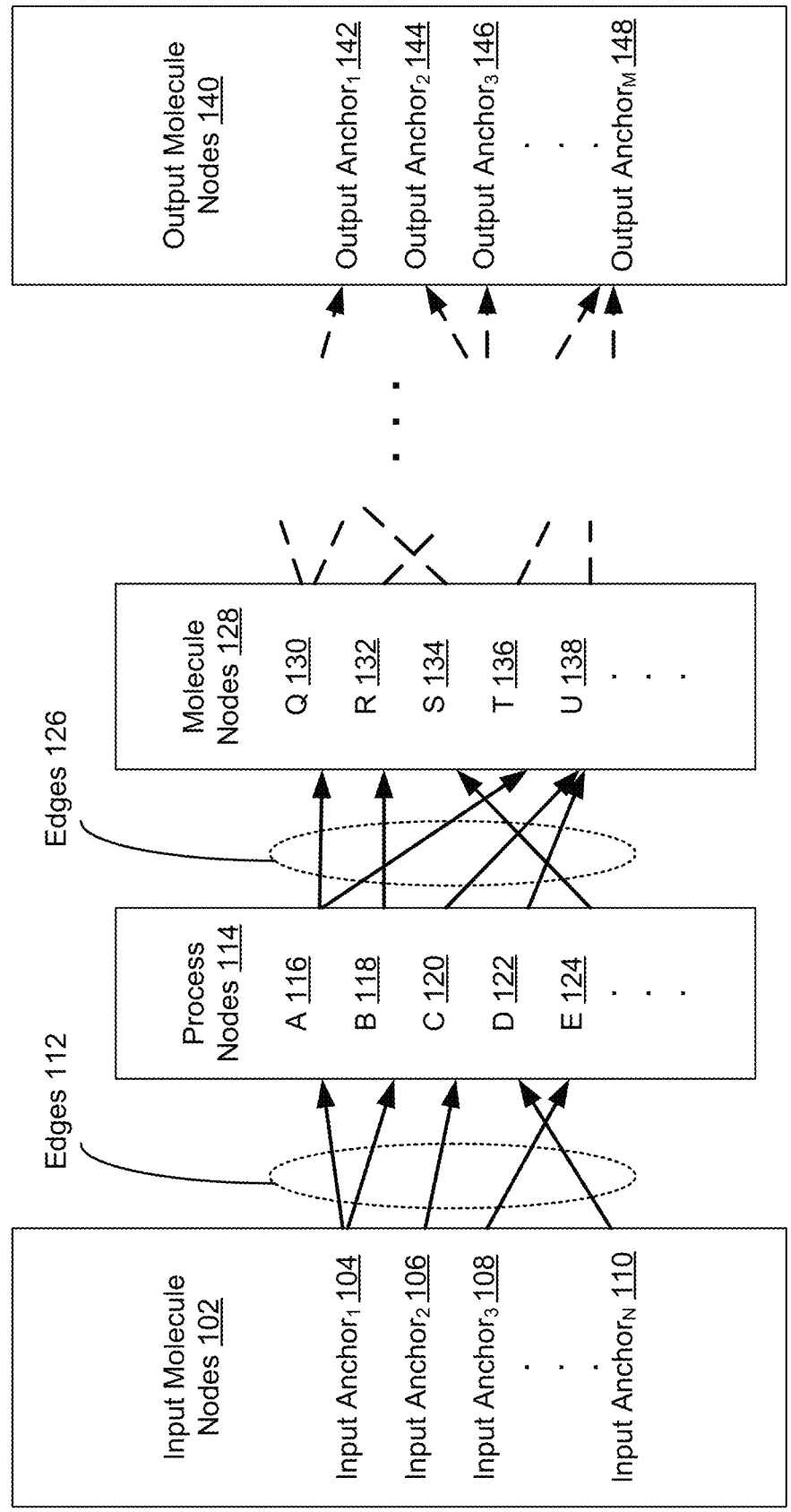
FIG. 1 is a block diagram illustrating a metabolic network structured as a bipartite graph, according to one embodiment.

A cell's metabolic system can be conceptualized as a linked network of pathways between reactants and products. This linked network can be structured as a bipartite graph data structure between two distinct sets of nodes. The first are molecule nodes representing molecules within metabolism, and the second are process nodes representing biochemical processes or reactions that may involve multiple molecules in distinct roles. Edges in the bipartite graph connect molecule nodes to the process nodes representing the reactions in which they participate. Edges store information about the role the molecule node plays in the reaction of the process node. As described herein, a metabolic "pathway" as represented in the bipartite graph is a path traversable between molecule nodes and process nodes along their connected edges (e.g., a first molecule node, a first role edge, a first process, a second role edge, a second molecule, etc.) By linking all metabolic inputs and metabolites in the bipartite graph, a cell's entire metabolic system can be converted to a reaction network of nodes and edges, whose structure reflects the biochemical relation between each molecule and process in the network.

Mathematical simulations of metabolic networks focus on solving for the concentrations of molecules within the network, the logic being that behavior of biochemical processes are reflected by the buildup or reduction in the molecules involved in the biochemical process. For example, if a biochemical process occurs frequently, this behavior may translate to a decrease in concentration of reactant molecules, and an increase in concentration of product molecules. Thus while a metabolic network is made up of both molecules and processes, the unknown variables in the mathematical simulation of the network can be restricted to a set of unknown molecule concentrations without loss of information, since the concentrations implicitly describe the processes.

A bipartite graph data structure works well for use in computational simulations of the metabolic network, since the graph stores each of the variables (e.g., molecules and processes) and their relative relationships (e.g., the edges) within the data structure. Computational simulations of metabolism can be used alone, or in conjunction with models of other cellular processes, such as gene expression, DNA repair, cellular communication, etc. to construct a "whole cell" computational model.

However, even for simple organisms, the number of nodes and edges in a metabolic system can range from high hundreds to low thousands. To build the bipartite graph, a number of sources may be referenced to identify the molecules, enzymes, cofactors, etc. that make up a cell's metabolic network. These sources may include primary literature, databases, biochemistry textbooks, conference presentations, or any other primary source literature. The contents of the bipartite graph may be manually populated to form the metabolic network in a bipartite graph data structure. Once a full bipartite graph of a metabolic system is built, the sheer size makes it computationally unwieldy, resulting in long run-times and reduced ease-of-use of the simulation. Furthermore, because pathways are often pulled from a variety of sources, it is difficult to assess the correctness of the network with more than a few tens of compounds. For example, a metabolic pathway from one primary source may have redundant portions of its pathway to another metabolic pathway, resulting in unnecessary additional computation. However, because of the size of the network, this redundancy may not be easily identified.

Similarly, the size of the bipartite graph makes it difficult to identify the relative importance of each pathway to the metabolic network, or of any individual molecule node, process node, or edge. For example, a particular metabolic pathway may not substantially contribute to the functioning of metabolism, and could be removed or blocked without affecting the mathematical simulation of the metabolic network. In contrast, other metabolic pathways may be crucial, such that any change to a node or edge in the pathway leads to the breakdown of the mathematical simulation. Particularly when the metabolic network is integrated with other sub-units representing other cellular processes, the relative importance of portions of the metabolic network may not be evident. For example, a molecule represented by a molecule node may be used in other sub-units outside metabolism, a relationship which may not be immediately evident upon construction of the initial bipartite graph from primary sources. As another example, portions of the metabolic network may not significantly contribute to mathematical solutions to a metabolic simulation, but may contain important precursors used in other cellular processes as represented in other mathematical molecules, such that blocking or removing them from the bipartite graph would affect the whole cell model.

Mathematical simulations of metabolism that use the bipartite graph data structure may be stoichiometric mass balance models that relate quantities of molecules represented by molecule nodes in reaction pathways. In these models, the stoichiometric coefficients of each reaction pathway between the molecule nodes of the bipartite graph function as reaction constraints, where the stoichiometry of each reaction is fixed by elemental and charge balance and are therefore fully time independent. Stoichiometric mass balance models may be used with flux balance analysis (FBA), ordinary differential equation (ODE) models, partial differential equation (PDE) models, Monte Carlo simulations, or some combination of these. These mathematical simulations result in a solution space of possible molecule concentrations given the mass balance constraints between molecule nodes in reaction pathways and the overall network structure given by the bipartite graph.

These stoichiometric mass balance models assume steady state solutions when solving for molecule concentrations. In FBA for example, the model can also assume that the flux through a "biomass" function (represented by the stoichiometric coefficients of an objective function) will be mathematically maximized, an assumption interpreted to mean that the cell will maximize growth. Thus the FBA maximizes the objective function given the constraints of the stoichiometric coefficients, and given the relative relationship among molecule nodes and process nodes as stored in the bipartite graph. The assumptions of FBA allow for exact, single solutions to the steady state flux through each metabolic pathway to be determined. ODE, PDE, and/or Monte Carlo models may also assume related or similar steady state solutions. Each of these models may be configured to maximize an objective function of flux values, or an equivalent, or configured to be run with respect to some other objective function, such as an object function that maximizes a value other than biomass.

There is a need for a way of reducing the computational complexity of mathematically simulating metabolic networks, as well as simplifying the network to better identify the relative importance of various metabolic pathways. Using the bipartite graph in the context of mathematical models that assume steady state solutions (such as FBA) provides a mathematical criteria and rationale for reducing the number of pathways in the metabolic network, and their corresponding nodes and edges in the bipartite graph. Following the criteria of FBA and other steady-state mathematical models with steady state assumptions allows the bipartite graph to be reduced without affecting the mathematical simulation of a metabolic network.

II. Significance of Zero Flux Pathways

Using FBA as a prototypical example, mathematically relevant pathways of the bipartite graph are those that have a flux value at a steady state of the system after a FBA simulation is run. This means that, at steady state, the metabolic pathway has a non-zero flux into the pathway, and a non-zero flux out of the pathway. Biologically, this is interpreted to mean that the pathway takes in molecules from outside the metabolic network, and outputs molecules to other parts of the cell outside of the metabolic network, at steady state of the system. While there may be intermediate molecules and nodes in the pathway, FBA flux value solutions only provide values for the inputs and outputs of the metabolic network at the boundaries of metabolism.

Thus, if, at steady state, the flux through a metabolic pathway is zero, the pathway may be blocked from the bipartite graph without affecting the solutions of FBA. Any time-intermediate behavior of the flux values (representing build-up of a product, consumption of a product, etc.) that occur before steady state is reached are not relevant to the mathematical simulation of metabolism under these steady state assumptions. Metabolic pathways with zero flux may therefore be thought of as "dead-end" pathways.

Analyzing the structure of the bipartite graph representation of the metabolic network provides a way to identify dead-end, zero flux pathways. To have a non-zero flux, and thus to contribute to the solutions of FBA or any other mathematical model with steady state assumptions, each reactant is converted into a product, such that the pathway spans the full length of the metabolic network from an input boundary to an output boundary. As reflected in the bipartite graph, this translates to the requirement that all molecule nodes contain at least one edge leading into the molecule node, and at least one edge leading out of the molecule node. In contrast, a dead-end zero flux pathway will have at least one molecule node that does not have an edge leading into the molecule node, or an edge leading out of the molecule node.

The fact that dead-end pathways lead to zero flux is a direct result of steady-state and mass balance assumptions. If a molecule node has no edges leading into it, or no edges leading out of it, then the only possible solution to a requirement that the sum of flux values at the molecule node be zero is for any connected edges to have zero flux. For example, if a molecule has no edges leading into it, but one edge leading out, the only solution that produces a net zero flux is for the flux value of the edge leading out of the molecule node to be zero. Zero flux pathways can thus be identified by calculating the number of edges in the bipartite graph that connect in to a particular node, and the number of edges in the bipartite graph that connect out from a particular node.

Once identified, the bipartite graph may be simplified by blocking the molecule nodes and edges associated with the dead-end zero flux pathways. Further checks may be added to confirm that the molecule nodes and edges can be blocked in the bipartite graph without significantly affecting the mathematical simulation of the metabolic network, such as the flux value solutions of FBA.

III. Significance of Intermediate Pathways

In addition to the dead-end pathways, the bipartite graph may be further simplified under the criteria of FBA. Because FBA solutions only give the vector solutions for the inputs and outputs of metabolism, intermediate molecule nodes within the network are only relevant to FBA solutions insofar as they preserve the reaction pathway between the input flux at the input boundary and the output flux at the output boundary. For example, in a pathway with 20 intermediate molecule nodes between a first node and a final node, the 20 intermediate molecule nodes will not contribute to the input flux leading into the first node or the output flux leading out of the final node. The bipartite graph can be simplified by removing the 20 intermediate molecule nodes, provided they do not influence any other pathway.

Analyzing the structure of the bipartite graph provides a way to identify intermediate molecule nodes. An intermediate molecule node contains one edge leading into the molecule node, and one edge leading out of the molecule node. With some exceptions described below, the bipartite graph can be simplified by removing the molecule nodes and edges associated with identified intermediate molecule nodes without significantly affecting the mathematical simulation of the metabolic network, such as the flux vector solutions of FBA.

Further embodiments of analyzing the bipartite graph structure to simplify a metabolic network are described in greater detail below.

IV. Metabolic Network As a Bipartite Graph

FIG. 1 is a block diagram illustrating a metabolic network structured as a bipartite graph, according to one embodiment. As previously described, the bipartite graph consists of two distinct sets of nodes, molecule and process, which are connected by edges. However, as shown in FIGS. 1-10C, the bipartite graph has been expanded to better visualize the structure of the metabolic network. It is to be understood that the molecule nodes shown herein are all contained within a first set, whereas the process nodes shown herein are all contained within a second set. The edges shown herein connect molecule nodes in the first set to process nodes in the second set.

The expanded bipartite metabolic network 100 includes input molecule nodes 102. The input molecule nodes 102 represent the input molecules of metabolism, and are the input boundary of the bipartite metabolic network 100. Each of the input molecule nodes 102 is connected to at least one of the process nodes 114 by edges 112. Each of the process nodes 114 are connected to molecule nodes 128 by edges 126.

Thus each of the input molecule nodes 102 is connected to at least one of the molecule nodes 128 through the process nodes 114 and edges 112 and 126. The molecule nodes 128 represent the first products of metabolism. Depending on the number of molecule and process nodes in the pathways of the bipartite metabolic network 100, there may be any number of additional molecule nodes and edges in the expanded bipartite metabolic network 100 showing the reaction pathways from input molecule nodes 102 to output molecule nodes 140. The output molecule nodes 140 represent the outputs of metabolism, and are the output boundary of the bipartite metabolic network 100.

A. Scope of Bipartite Metabolic Network

The expanded bipartite metabolic network 100 includes all molecules and processes that are used in a steady-state mathematical simulation of a metabolic network. For example, the bipartite metabolic network 100 contains all molecules and processes used in a FBA model of a metabolic network. In some examples, a metabolic network is simulated using multiple mathematical sub-units, each of which models a different portion of the metabolic network. In some examples, a steady state assumption is not made for all mathematical sub-units. In these examples, the expanded bipartite metabolic network 100 may only contain molecules and processes that are included in sub-units with steady state assumptions. In other examples, the expanded bipartite metabolic network 100 contains all molecules and processes of a metabolic network, and only a portion of the expanded bipartite metabolic network 100 used in mathematical models with steady state assumptions is simplified and condensed as described below.

B. Process Nodes in the Bipartite Graph

As described herein, process nodes, such as process nodes 114, describe molecular actions in a biochemical environment including but not limited to chemical reactions, regulatory interactions, binding, transport, or others. Thus each of the process nodes 114, process node A 116, process node B 116, process node C 120, process node D 122, and process node 124, each describe a different molecular action within the expanded bipartite metabolic network 100. A process node includes a number of descriptive metadata fields that provide information about the process including but not limited to a list of molecules and their associated roles in the process, reaction rate information, and energy requirements for the process, sub-processes that may be involved in the process, or other more detailed information.

C. Molecule Nodes in the Bipartite Graph

As described herein, within a metabolic network structured as a bipartite graph, molecule nodes, such as input molecule nodes 102, molecule nodes 128, and output molecule nodes 140 are nodes of the bipartite graph that represent a molecule or chemical element that is present in metabolism. Input molecule nodes 102, molecule nodes 128 and output molecule nodes 140 are understood to be contained together within the molecule node set of the bipartite graph, but are shown in the expanded bipartite metabolic network 100 as separate to show the reaction pathway between input molecule nodes 102 and output molecule nodes 140. A molecule node may represent small molecules such as water, carbon dioxide, protons, etc. or macromolecules such as proteins, lipids, alcohols, organic acids, vitamins, etc. As stored in the bipartite metabolic network 100, a molecule node may contain a plurality of metadata fields describing the molecule. The metadata of a molecule node may include the molecule name, a molecule formula, an amino acid sequence, a macromolecular structure, electrical charge, chemical or physical properties (pKa, melting point, solubility, etc.) and any component molecules. Additionally, some non-physical properties may be included in the metadata of a molecule node including drug interaction, 3D structure etc. A molecule node need not contain information for each one of the previously described metadata categories.

D. Input Nodes of the Bipartite Graph

Input molecule nodes 102 represent molecules that are inputs to metabolism, and thus to the expanded bipartite metabolic network 100. The input molecule nodes 102 may include molecules that are inputs to metabolism from an upstream cellular process, as well as molecules in the cytoplasm of a cell, and molecules that the cell model is capable of sourcing from its external environment and using in a metabolic network. All of the input molecule nodes 102 and input anchors have an input flux value solution. The input flux value solutions for the input molecule nodes 102 may be determined by solving an FBA model using the expanded bipartite metabolic network 100. The input flux value solution for a molecule node in the expanded bipartite metabolic network 100 represents the rate at which that molecule enters the metabolic network at steady state of the metabolic system. The input flux of a molecule node can be conceptualized as the metabolic "demand" for the molecule. In some examples, the flux value solutions of all input anchors and input molecule nodes 102 are non-zero. In other examples, input flux value solutions for a subset of the input molecule nodes 102 and input anchors are 0.

Molecules that are input molecule nodes 102 are "anchored" within the expanded bipartite metabolic network 100 and stored within the input molecule nodes 102 as input $anchor_1$ 104, input $anchor_2$ 106, input $anchor_3$ 108 through input $anchor_N$ 110, where N is the total number of input molecule nodes 102. As used herein, "anchored" nodes (such as input $anchor_1$ 104, input $anchor_2$ 106, input $anchor_3$ 108 through input $anchor_N$ 110) are molecule nodes that are always included in FBA analysis of the expanded bipartite metabolic network 100. As such, they are isolated from the rest of an expanded bipartite metabolic network 100 when the expanded bipartite metabolic network 100 is simplified and condensed, as described in further detail with reference to FIG. 6-10C. As described above the molecules represented by the input anchors input $anchor_1$ 104, input $anchor_2$ 106, input $anchor_3$ 108 through input $anchor_N$ 110 need not be present within the cell during mathematical simulations using the expanded bipartite metabolic network 100.

In an example, the input $anchor_1$ 104 represents a molecule that is a direct input to a cell's metabolism from an upstream cellular process. For example, the upstream cellular process may be transcription, such that the input $anchor_1$ 104 molecule is an RNA molecule previously used in the cell and that is then broken down in the cell's metabolism. The input $anchor_1$ 104 has an input flux value solution, as calculated from a mathematical model of the expanded bipartite metabolic network 100, such as a FBA model. Input $anchor_1$ 104 is thus at the "boundary" to the expanded bipartite metabolic network 100, and enters the expanded bipartite metabolic network 100 at a rate given by its input flux value solution, representing the metabolic rate of consumption of RNA.

In another example, the input $anchor_2$ 106 is a direct input to a cell's metabolism, however it is not present within an upstream cellular process and is instead sourced by the cell through a membrane transport pathway, or some other cellular mechanism. In some examples, input $anchor_2$ 106 may be any of: glucose, water, an amino acid, or any other input to metabolism. The input $anchor_2$ 106 may not have a concentration within the cell during mathematical simulation of the expanded bipartite metabolic network 100. Alternatively, the input $anchor_2$ 106 may be present in the environment outside of the cell, and through a membrane transport pathway, the cell delivers the input $anchor_2$ 106 to the expanded bipartite metabolic network 100. The input $anchor_2$ 106 may contain metadata linking it to the membrane transport pathway, or other cellular mechanism from which it is sourced to the expanded bipartite metabolic network 100.

In another example, the input $anchor_3$ 108 may have a constant or near-constant presence within the cytoplasm of the cell, such that the molecule of the input $anchor_3$ 108 is stored at some concentration external to the metabolic network, but within the cell model. The input flux of the input $anchor_3$ 108 thus represents a movement of the input $anchor_3$ 108 from the cell's storage concentration to the expanded bipartite metabolic network 100.

E. Edges Linking Nodes

Edges link molecule nodes, such as the input molecule nodes 102, to process nodes, such as process nodes 114 in a bipartite graph. For example, edges 112 connect input molecule nodes 102 to process molecule nodes 114. Specifically, a single edge 112 connects a single input molecule node 102 to a single process node in the process nodes 114. Each edge in the edges 112 represents the role of the input molecule of the input molecule nodes 102 in the biochemical process represented by the process nodes 114. For example, as shown in the expanded bipartite metabolic network 100, the input anchor$_1$ 104 is connected by an edge in the edges 112 to process A 116 in the process nodes 114. This edge represents a chemical reaction or process in which the input anchor$_1$ 104 is a reactant, where the process is process A and the role of input anchor$_1$ 104 is represented by the edge.

The direction of the edges 112 (e.g., pointing from input molecule nodes 102 to first molecule nodes 114) indicates the direction of a chemical reaction. Thus an edge pointing from a first molecule node to a process node, and from the process node to a second molecule node indicates that the first molecule is a reactant and the second molecule is a product in the chemical reaction represented by the process node. As described herein, an edge "leading out" of a molecule node indicates that a chemical reaction uses that molecule as a reactant, and that the direction of the chemical reaction in the metabolic network is forward, away from that molecule. As described herein, an edge "leading into" a molecule node indicates that a chemical reaction produces that molecule as a product, and that the direction of the chemical reaction in the metabolic network is forward toward that molecule. For example, edges 112 lead out of the input molecule nodes 102, indicating that these are reactant molecules, and edges 126 lead into molecule nodes 128, indicating that these are product molecules.

The expanded bipartite metabolic network 100 then includes molecule nodes 128, which are shown connected to process nodes 114 with edges 126. The input molecule nodes 102 may be reactants in chemical reactions represented by the process nodes 114 that then produce molecule nodes 128 as products. The edges 126 indicate which of the molecule nodes 128 are produced in which of the process nodes 114, as well as the direction of the chemical reactions. Not all of the molecule nodes 128 may be used in subsequent process nodes (not shown). This may be due to some of the molecule nodes 128 being unused or unmade molecule nodes. Unused and unmade molecule nodes are described in further detail with reference to FIGS. 6, 7 and 9-10C. In some examples, some of the molecule nodes 128 may be reactants in chemical reactions that produce the input molecule nodes 102 as products, such that the edges 126 lead out of these molecule nodes 128 and into the process nodes 114, and some of the edges 112 lead out of the process nodes 114 and into the input molecule nodes 102. This may be due to cyclical portions of the expanded bipartite metabolic network 100 and/or one of the molecule nodes 128 being orphan molecule nodes. Orphan molecule nodes are described in further detail with reference to FIG. 5. In any case, the relation between input molecule nodes 102, process nodes 114 and molecule nodes 128 will be indicated in the expanded bipartite metabolic network 100 by the edges, such as edges 112 and 126.

For example, as shown in FIG. 1, process A 116 is a biochemical process that produces two output molecules represented by two separate edges in the edges 126, and takes as input a single molecule, input anchor$_1$ 104, which is connected to process A 116 by a single edge in the edges 112. Process A 116 is connected to molecule Q 130 in the molecule nodes 128. Process A 116 is also connected to molecule T 136 in the molecule nodes 128 by a second edge in the edges 126. Thus the structure of the expanded bipartite metabolic network 100 indicates the biochemical relation between molecule nodes and process nodes within metabolism.

Edges 112 and 126 may store metadata further specifying the details of the role connected molecules play in connected processes within the expanded bipartite metabolic network 100. For example, edges 112 and 126 include the stoichiometric balance between connected molecules and processes. The edge connecting process A 116 and molecule Q 130 includes the stoichiometry of the reaction producing molecule Q 130. The edges 112 and 126 may also include the enzymes, cofactors, or other facilitating molecules involved in a chemical reaction. Edges 112 and 126 may include protein folding operations and the movement of these facilitating molecules in the cell, as well as rates and locations and numbers of active sites. Additionally or alternatively, edges 112 and 126 store activation energy, Gibbs free energy change, kinematic properties and other thermodynamic properties known in the art describing the chemical reaction. Edges 112 and 126 may store this and any additional information relevant for describing the chemical reactions or processes that convert molecule nodes from reactants to products within the expanded bipartite metabolic network 100.

Edges 112 and 126 have associated flux values, which are rates at which molecule nodes are used in processes, however, since these edges are not at the boundaries of metabolism, they may not be solved for in an FBA model using the expanded bipartite metabolic network 100. The direction of flux through the expanded bipartite metabolic network 100 and between molecule nodes and process nodes is indicated by the direction of the edge. For example, the edge leading out of process A 116 and into molecule Q 130 has an associated flux rate, which indicates the rate at which process A 116 produces molecule Q 130. The flux values of the input anchors are the input flux values of the bipartite metabolic network 100, and may be determined through a mathematical simulation of the bipartite metabolic network 100, such as an FBA model simulation.

F. Output Nodes of the Bipartite Graph

There may be any number of molecule and process nodes within the expanded bipartite metabolic network 100. Ultimately, the expanded bipartite metabolic network 100 ends with the output molecule nodes 140. Output molecule nodes include any number of output anchor molecules, such as output anchor$_1$ 142, output anchor$_2$ 144, output anchor$_3$ 146 through output anchor$_M$ 148, where M is the total number of output molecules of the expanded bipartite metabolic network 100. Each of the output molecule nodes 140 represent the outputs of metabolism as shown as the expanded bipartite metabolic network 100. The output molecule nodes 140 may thus be used in cellular processes downstream from metabolism, stored within the cell, output through a membrane transport pathway, and/or any other use in the cell external to metabolism. Each of these cellular processes may have their own associated mathematical model and simulation. Cellular processes external to metabolism within a full cell mathematical model are described in further detail with reference to FIG. 11.

All of the output molecule nodes 140 and output anchors have an output flux value solution. The output flux value solutions for the output molecule nodes 140 may be determined by solving an FBA model using the expanded bipartite metabolic network 100. The output flux value solution for a molecule node in the expanded bipartite metabolic network 100 represents the rate at which that molecule leaves the metabolic network at steady state of the metabolic system. The output flux of a molecule node can be conceptualized as the metabolic "production" of the molecule. In some examples, the flux value solutions of all output anchors and output molecule nodes 140 are non-zero. In other examples, output flux value solutions for a subset of the output molecule nodes 140 and output anchors are 0.

Each of the output molecule nodes 140 are designated as "anchored" nodes. Thus output anchor$_1$ 142, output anchor$_2$ 144, output anchor$_3$ 146 through output anchor$_M$ 148 are isolated from the rest of an expanded bipartite metabolic network 100 when the expanded bipartite metabolic network 100 is simplified and condensed, as described in further detail with reference to FIG. 6-10C. Not all of the output anchors need be produced during a given simulation of the expanded bipartite metabolic network 100, however at least one reaction pathway within the expanded bipartite metabolic network 100 must be capable of producing the output molecule nodes 140 as its final product. Thus at least one edge in the bipartite metabolic network leads into each of the output molecule nodes 140.

Input molecule nodes 102, molecule nodes 128, and output molecule nodes 140 are stored together as a first set in the bipartite graph. They may each be stored as an array, or in any other data structure known in the art. Input molecule nodes 102, edges 112, process nodes 114, edges 126, molecule nodes 128, and output molecule nodes 140 are populated into the expanded bipartite metabolic network 100 as molecule nodes and process nodes from a variety of sources, such as primary literature, databases, biochemistry textbooks, conference presentations, or any other primary source literature. As initially input into the expanded bipartite metabolic network 100, there may be redundancies in the expanded bipartite metabolic network 100, or reaction pathways between molecule nodes that are dead-ends, such that at steady state of the expanded bipartite metabolic network 100, there is zero flux through the pathway.

The biochemical relation between all molecules and processes within a metabolic network are thus converted to a structure of edges, process nodes and connected molecule nodes to form the expanded bipartite metabolic network 100. To identify features of the metabolic network, such as the relative importance of reaction pathways, or dead-end pathways, one can analyze the structure of the expanded bipartite metabolic network 100. Specifically, the biochemical relation of each molecule and its corresponding molecule node to other molecules and molecule nodes is given by the edges into and out of each node. By categorizing molecule nodes according to the number of edges into and out of each node, the bipartite metabolic network 100 can be condensed and simplified, and important reaction pathways identified. Classification of molecule nodes within the bipartite metabolic network 100 is described below in further detail with reference to FIG. 2-10C.

V. Confluence Node

FIG. 2 is an illustration of confluence 200 in a metabolic network, according to one embodiment. As shown in FIG. 2, node 206 is a confluence node. A confluence node is any molecule node in a bipartite graph (such as the bipartite metabolic network 100) that has a plurality of edges leading into the node, and a single edge leading out of the node. For example, three process nodes 202 each have a connected edge in the edges 204 leading into node 206. Each of the process nodes 202 is thus a chemical reaction or process that has molecule node 206 as a product. A single edge 208 leads out of molecule node 206. The edge 208 leads into process node 210. Edge 208 represents the participation of molecule node 206 as a reactant in the process represented by process node 210. As an example, Xanthosine 5'-phosphate (XMP) would be represented as a confluence node in a bipartite graph is since it may be produced through two separate chemical reactions, and is consumed by a single reaction.

Molecule nodes in a bipartite graph are categorized as confluences 200 when the number of edges leading into the node is greater than one, and the number of edges leading out of the node is one. By counting the number of edges leading into and leading out of each molecule node in a bipartite graph, a confluence 200 can be identified and categorized within the bipartite graph.

VI. Fork Node

FIG. 3 is an illustration of a fork 300 in a metabolic network, according to one embodiment. As shown in FIG. 3, node 306 is a fork node. A fork node is any molecule node in a bipartite graph (such as the expanded bipartite metabolic network 100) that has a single edge leading into the node, and a plurality of edges leading out of the node. For example, edge 304 leads out of process node 302 and into molecule node 306. Edge 304 thus represents the production of molecule node 306 from a single chemical reaction of process node 302. Edge 304 is the only edge leading into node 306. A plurality of edges 308 lead out of molecule node 306 and into process nodes 310. Thus node 306 is a reactant in each of the chemical reactions represented by process nodes. As an example, UDPglucose would be represented as a fork node in a bipartite graph since it is made from both UTP and glucose, but is a reactant in a number of downstream chemical reactions in metabolism.

Molecule nodes in a bipartite graph are categorized as forks 300 when the number of edges leading into the molecule node is one, and the number of edges leading out of the molecule node is greater than one. By counting the number of nodes leading into and leading out of each molecule node in a bipartite graph, a fork 300 can be identified and categorized within the bipartite graph.

VII. Nexus Node

FIG. 4 is an illustration of a nexus 400 in a metabolic network, according to one embodiment. As shown in FIG. 4, node 406 is a nexus. A nexus 400 is any molecule node in a bipartite graph (such as expanded bipartite metabolic network 100) with a plurality of edges leading into the molecule node, and a plurality of edges leading out of the molecule node. For example, each of the three process nodes 402 have an edge in edges 404 leading out of the process node and leading into molecule node 406. Thus each of the process nodes 402 are chemical reactions that produce molecule node 406 as a product. Molecule node 406 is a reactant in the three chemical reactions represented by process nodes 410. Each of the edges 408 leads out of molecule node 406 and into one of the process nodes in process nodes 410. Thus each of the process nodes 410 is a chemical reaction in which molecule node 406 is a reactant. As an example, ATP and other common cofactors of metabolism would be represented as nexus nodes in a bipartite graph since a number of reactions produce it, and a number of reactions consume it.

Molecule nodes in a bipartite graph are categorized as a nexus 400 when a number of edges leading into the molecule node is greater than one, and a number of edges leading out of the molecule node is also greater than one. By counting the number of edges leading into and leading out of each molecule node in a bipartite graph, a nexus 400 can be identified and categorized within the bipartite graph.

VIII. Orphan Node

FIG. 5 is an illustration of an orphan 500 in a metabolic network, according to one embodiment. As shown in FIG. 5, node 508 is an orphan. An orphan 500 is any molecule node in a bipartite graph (such as bipartite metabolic network 100) with a single edge leading into the molecule node, a single edge leading out of the molecule node, and both edges lead into and out of the same process node. This means that an orphan node is a product and also a reactant for aprocess. For example, edge 504 leads out of process node 502 and into molecule node 508. Thus process node 502 is a single chemical reaction that produces molecule node 508. Edge 506 leads out of molecule node 508 and into process node 502. Thus molecule node 508 is a reactant in a single chemical reaction represented by process node 502. As an example, oxidized glutathione may be represented as an orphan in a bipartite graph, since it is a product of a reversible Glutathione Peroxidase reaction, but is not subsequently used in a downstream chemical reaction.

Molecule nodes in a bipartite graph are categorized as orphan 500 when the number of edges leading into the molecule node is one, the number of edges out of the molecule node is one, and the leading and entering nodes go to the same process node. By counting the number of nodes leading into and out of each molecule node in the bipartite graph, and checking if they are connected to the same second molecule, an orphan 500 can be identified and categorized within the bipartite graph.

IX. Unused Nodes

Figure 6:
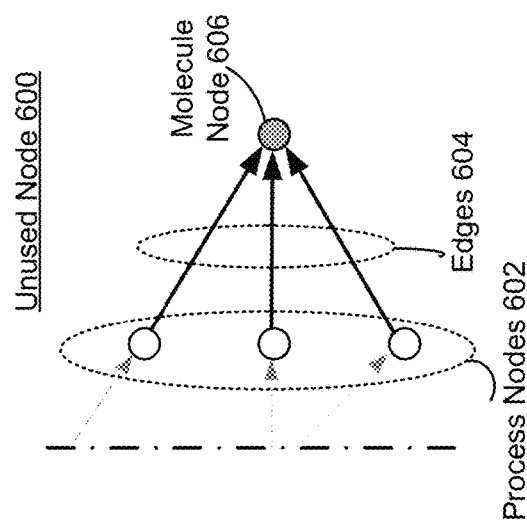
FIG. 6 is an illustration of an unused node in a metabolic network, according to one embodiment.

FIG. 6 is an illustration of an unused node 600 in a metabolic network, according to one embodiment. As shown in FIG. 6, molecule node 606 is an unused node. An unused node is any molecule node in a bipartite graph (such as expanded bipartite metabolic network 100) with zero edges leading out of the node. The biological interpretation for having no edges leading out of an unused node is that the unused node is not consumed or used in any chemical reactions or processes. For example, process nodes 602 are each biochemical processes that produce molecule node 606, as represented by edges 604. Each of the edges 604 lead out of a process node in process nodes 602 and into molecule node 606. However, molecule node 606 does not have any edges leading out of it, and is therefore not a reactant in any chemical reaction in the bipartite graph. As an example, reduced ferredoxin may be represented as an unused node in a bipartite graph, since it is produced by an irreversible reaction and not subsequently used within metabolism.

The consequence of being "unused" and is that molecule node 606 may result in some portion of the bipartite graph becoming a dead-end, or associated with zero flux values at steady state. Because the number of edges leading out of an unused node is zero, the structure of the bipartite graph indicates that the node is unused, and has zero flux. However, it is possible that due to other connections between the molecule and other processes outside of metabolism, or due to inaccuracies or incompleteness of the bipartite graph, the molecule node will have non zero flux, affect the flux values of other molecules, and/or affect the overall growth rate of the cell. Solving for the flux values, as well as running mathematical simulations of a cell model will confirm each of these checks. However, categorization of the molecule as unused by analyzing the structure of the bipartite graph flags the molecule node for potential blocking following these further checks. These are described in further detail with reference to FIG. 9B.

If the unused node does in fact have zero flux, the unused molecule node 606 prevents the reaction pathways it is connected to from spanning the bipartite graph from an input anchor to an output anchor. Thus the reaction pathway in which it is connected does not have net flux or movement through the metabolic network at steady state. This affects the molecule and process nodes and edges connected to the unused molecule node 606. The total number of nodes and edges the unused molecule node 606 affects in the bipartite graph is dependent on the structure of the upstream portions of the bipartite graph that are connected to molecule node 606. As shown in FIG. 6, upstream reactions beyond process nodes 602 are not considered, but the full effects of the presence of an unused node 600 on upstream connected nodes and edges are described in further detail with reference to FIG. 9A-10C. In some examples, the presence of an unused node 600 in a reaction pathway may lead to blocking the reaction pathway.

In intermediate time scales, the reactions represented by process nodes 602 may occur, such that they produce molecule node 606. However, since molecule node 606 is not subsequently used in any reaction, any concentration of molecule node 606 produced by the reactions of process nodes 602 builds up in concentration in the reaction pathway, until it is no longer energetically favorable for the reactions represented by process nodes 602 to occur. In this example, at steady state, at least the edges 604 which are directly connected to the unused node 606 will have zero flux. It is possible that these zero flux edges 604 cause other connected upstream reaction pathways to also have zero flux at steady state. For example, if nodes upstream from the molecule node 606, such as process nodes 602, are not connected to any other reaction pathways in the bipartite graph and are only involved in the reaction pathway leading to the molecule node 606, then the build-up of molecule node 606 causes these other edges to have zero flux as well. This is described in further detail with reference to FIG. 9A-10C. In some cases, the molecule node 606 thus blocks all connected upstream reaction pathways (such as any nodes and edges connected to process nodes 602).

Because unused nodes, such as molecule node 606, result in at least the connected edges leading to the unused molecule node 600 having zero flux, in some cases unused nodes can be blocked from the bipartite graph without affecting the flux balance solutions determined through mathematical simulations using the bipartite graph. If molecule node 606 has zero flux, the chemical reactions represented by process nodes 602 do not occur at steady state. Therefore, despite the fact that molecule node 606, edges 604 and process nodes 602 are present in the bipartite graph, for the purposes of flux through the metabolic network at steady state, they do not contribute to the mathematical solutions of the mathematical model of metabolism, and thus are superfluous calculations and variables that add to the complexity of the bipartite graph. They may thus be blocked from the bipartite graph and from the mathematical calculations that solve for the flux value solutions without affecting these solutions. Prior to blocking an unused node, a reaction pathway may be initially blocked and a number of checks may be made to confirm that the unused node has zero flux, and does not affect other molecule flux values and/or other models within the full cell. These checks are described in further detail with reference to FIG. 9B.

Molecule nodes in the bipartite graph are categorized as unused when the number of output edges of a node is zero. The number of edges leading into the molecule node is not relevant to categorization of unused nodes. By counting the number of edges leading out of each molecule node in the bipartite graph, an unused molecule node 600 can be identified and characterized within the bipartite graph.

X. Unmade Nodes

Figure 7:
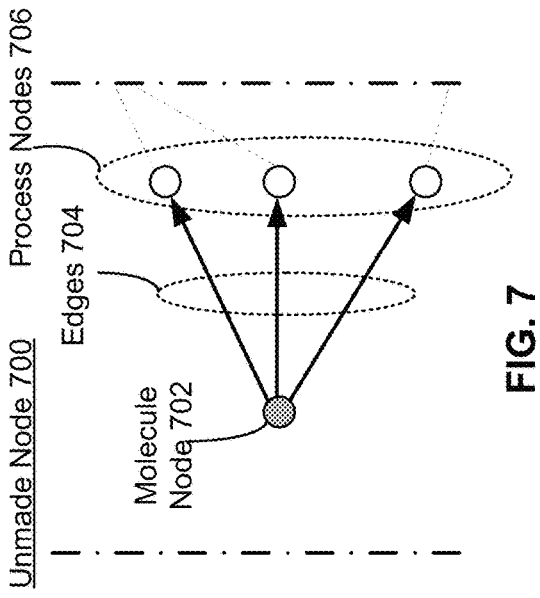
FIG. 7 is an illustration of an unmade node in a metabolic network, according to one embodiment.

FIG. 7 is an illustration of an unmade node 700 in a metabolic network, according to one embodiment. As shown in FIG. 7, molecule node 702 is an unmade node. An unmade node is any molecule node in a bipartite graph (such as expanded bipartite metabolic network 100) with zero edges leading into the node. The biological interpretation for having no edges leading into an unmade node is that the unmade node is not produced by any chemical reactions or processes within metabolism, nor is it an input to metabolism either from an upstream cellular process, storage within the cell, or through a membrane transport pathway from the cell's external environment. As an example, D-nopaline may be represented as an unmade molecule node in a bipartite graph since it is converted into arginine and 2-oxoglutarate, but there is no source for D-nopaline within metabolism.

For example, process nodes 706 are chemical reactions that use molecule node 702 as reactants, as represented by edges 704. Each of the edges 704 lead out of molecule node 702 and into process nodes 706. However, molecule node 702 does not have any edges leading into it, and is therefore not a product in any chemical reaction in the bipartite graph. Molecule node 702 is therefore categorized as "unmade."

The consequence of being "unmade" is that molecule node 702 may result in some portion of the bipartite graph becoming a dead-end, e.g., have zero flux values at steady state. Because the number of edges leading into an unmade node is zero, the structure of the bipartite graph indicates that the node is unmade, and has zero flux. However, similarly to the unused nodes, it is possible that due to other connections between the molecule and other processes outside of metabolism, or due to inaccuracies or incompleteness of the bipartite graph, the molecule node will have non zero flux, affect the flux values of other molecules and processes, and/or affect the overall growth rate of the cell. Solving for the flux values, as well as running mathematical simulations of a cell model will confirm each of these checks. However, categorization of the molecule as unmade by analyzing the structure of the bipartite graph flags the molecule node for potential blocking following these further checks. These are described in further detail with reference to FIG. 9B.

If the unmade node does in fact have zero flux, the unmade molecule node 702 prevents the reaction pathways it is connected to from spanning the bipartite graph from an input anchor to an output anchor. Thus the reaction pathway in which it is connected does not have net flux or movement through the metabolic network at steady state. This affects the molecule and process nodes and edges connected to the unmade molecule node 702. The number of nodes and edges the unmade molecule node 702 affects in the bipartite graph is dependent on the structure of the downstream connected portions of the bipartite graph. As shown in FIG. 7, downstream reactions beyond process nodes 706 are not considered, but the full effects of the presence of an unmade molecule node 702 on downstream connected nodes and edges are described in further detail with reference to FIG. 9A-10C. In some examples, the presence of an unmade molecule node 702 in a reaction pathway may lead to the blocking the reaction pathway.

If the unmade molecule node 702 does have zero flux, the immediate effect of the unmade molecule node 702 on the portion of the bipartite graph as shown in FIG. 7 is that, at a steady state of the metabolic network in which the molecule node 702 is located, the connected edges 704 have flux values of zero. At least the reaction pathways between molecule node 702 and process nodes 706 become dead-ends of the bipartite graph. At intermediate time scales, it is possible that some concentration of the molecule represented by molecule node 702 exist in the cell, and that they are used in the reactions represented by process nodes 706. However, because molecule node 702 is unmade, and therefore not created within metabolism, and not received from outside metabolism as one of the input molecule nodes of the bipartite graph (such as input molecule nodes 102 as described in further detail with reference to FIG. 1) at steady state the reactions represented by process nodes 706 will no longer occur, because either the molecule 702 is not present, or any small concentration has been used up at intermediate time scales. The edges 704 therefore have zero flux at steady state. Depending on the downstream structure of the bipartite graph, the zero flux of edges 704 may affect the process nodes 706. For example, if process nodes 706 are connected to other portions of the bipartite graph with non-zero flux values, then they will contribute to the flux value calculations and are kept within the bipartite graph. However, if process nodes 706 are not connected to other portions of the bipartite graph with non-zero flux values, then the zero-flux edges 704 will result in process nodes 706 also having zero-flux. The effect of unmade nodes 700 on larger portions of the bipartite graph are described in further detail with reference to FIG. 9A-10C.

Because unmade nodes, such as molecule node 702, result in at least the connected edges leading out of the unmade node 700 having zero flux, in some cases unmade nodes can be blocked in the bipartite graph without affecting the flux balance solutions determined through mathematical simulations using the bipartite graph. Since molecule node 702 has zero flux, the chemical reactions represented by process nodes 706 do not occur at steady state. Therefore, despite the fact that molecule node 702 and edges 704 are present in the bipartite graph, for the purposes of flux through the metabolic network at steady state, they do not contribute to the mathematical solutions of the mathematical model of metabolism, and thus are superfluous calculations and variables that add to the complexity of the bipartite graph. They may thus be blocked in the bipartite graph and in the mathematical calculations that solve for the flux value solutions without affecting these solutions. A number of checks may be made to confirm that the unmade node has zero flux, and does not affect other molecule flux values and/or other models within the full cell. These checks are described in further detail with reference to FIG. 9B.

Molecule nodes in the bipartite graph are categorized as unmade when the number of input edges of a node is zero. The number of edges leading out of the molecule node is not relevant to categorization of unmade nodes. By counting the number of edges leading into each molecule node in the bipartite graph, an unmade node 700 can be identified and characterized within the bipartite graph.

XI. Anchor Nodes Exempt From Categorization

When categorizing molecule nodes of a bipartite graph as an unused node 600 or unmade node 700, the anchors of the bipartite graph (e.g., the inputs to metabolism and outputs to metabolism) are not considered, and are exempt from categorization as unused or unmade. This ensures that the molecules at the interfaces of metabolism and the larger cellular environment are not removed or blocked within the bipartite graph. For example, as shown in FIG. 1, the input molecule nodes 102 are not considered unmade nodes, and output molecule nodes 140 are not considered unused nodes.

XII. Intermediates

Figure 8:
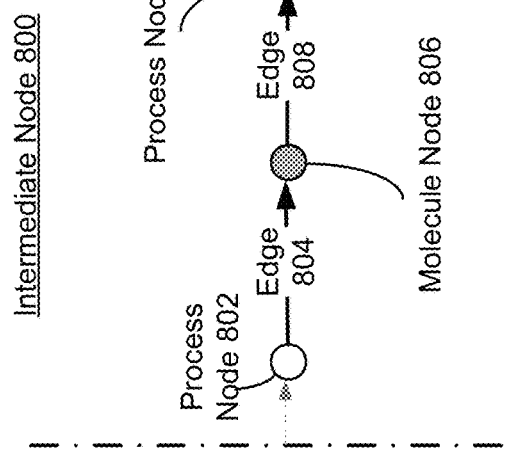
FIG. 8 is an illustration of an intermediate node in a metabolic network, according to one embodiment.

FIG. 8 is an illustration of an intermediate node 800 in a metabolic network, according to one embodiment. As shown in FIG. 8, molecule node 806 is an intermediate node. An intermediate node is any molecule node in a bipartite graph (such as expanded bipartite metabolic network 100) with one edge leading into the node and one edge leading out of the node. The biological interpretation of an intermediate is that the molecule of the intermediate node is only used as a precursor molecule between two other processes in a larger reaction pathway.

For example, intermediate molecule node 806 has a single edge 804 leading into it from process node 802. Intermediate molecule node 806 then has a single edge 808 leading out of it, and toward process node 810. Thus intermediate molecule node 806 is only used as an intermediate, precursor molecule between process node 802 and process node 810. While intermediate molecule node 806 may be biologically necessary to achieve this, for the purposes of a flux-based mathematical simulation of a bipartite graph, the molecule node 806 may be computationally irrelevant, and result in an unnecessary computational burden on the mathematical model.

When simulating metabolism using the bipartite graph within a FBA model, the FBA calculations solve for the flux values at the objectives of the metabolic network, meaning the flux values associated with input molecule nodes 102 and output molecule nodes 140, as shown in FIG. 1. The flux values that result from the presence of an intermediate molecule node 800 in a bipartite graph may not contribute to the FBA solutions. Intermediate molecule nodes can be removed from the bipartite graph to condense the reaction pathways and reduce the number of variables within the mathematical model. Thus removing the intermediate nodes 800 reduces the computational burden on the mathematical simulation, as well as condenses the metabolic network to better identify nodes that are crucial to the network and may be potential targets for disrupting or altering the metabolic network. Further details regarding the removal of intermediate nodes 800 are described with reference to FIG. 9A-10C.

Molecule nodes in the bipartite graph are categorized as intermediate nodes 800 when the number of input edges of a node is one and the number of output edges of a molecule node is one. By counting the number of edges leading into and out of each molecule node in the bipartite graph, an intermediate node 800 can be identified and characterized within the bipartite graph.

XIII. Simplification of Example Metabolic Network

Figure 9A:
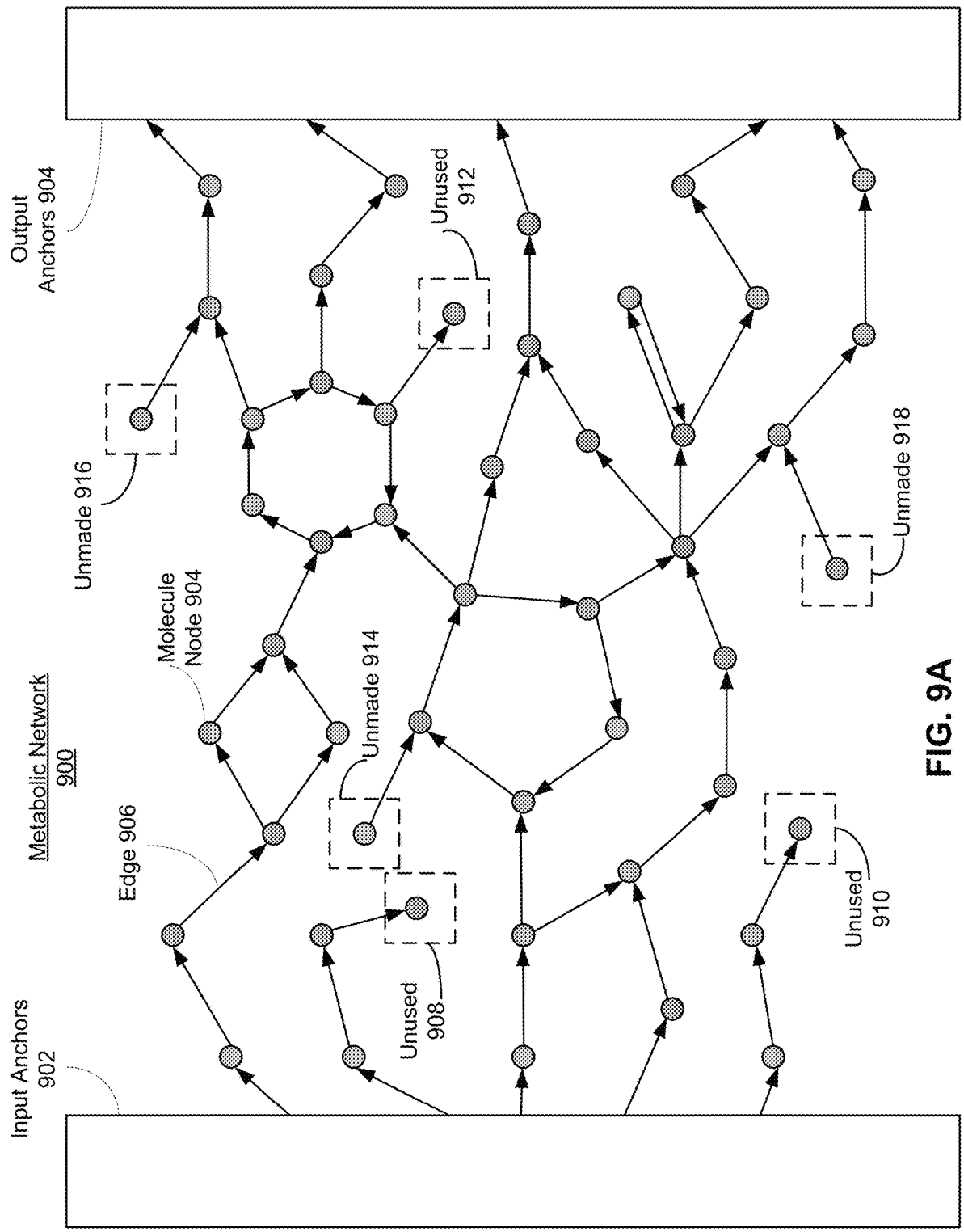
FIG. 9A is an abridged graphical representation of a metabolic network, according to one embodiment.

FIG. 9A is an abridged graphical representation of a metabolic network 900, according to one embodiment. FIG. 9A is described concurrently with the processes 1100 and 1200 of FIG. 11 and FIG. 12, respectively. The metabolic network 900 is a graphical representation of a metabolic network in a bipartite graph data structure. For example, the metabolic network 900 may be a graphical representation of the expanded bipartite metabolic network 100 as described in further detail with reference to FIG. 1. As shown in FIGS. 9A-10C, the metabolic network 900 has been abridged to include only molecule nodes, since it is on the basis of categorizing molecule nodes according to the categories of FIGS. 2-8 that decisions to simplify the metabolic network 900 are based. It is to be understood that the edges shown in FIGS. 9A-10C between molecule nodes represent biochemical processes, such that the number of edges leading into and out of molecule nodes in FIGS. 9A-10C are equivalent to the number of edges leading into and out of molecule nodes in the bipartite graph data structure of process nodes and molecule nodes. The abridgement of process nodes in the graphical representation of FIGS. 9A-10C simply streamlines the visual representation of the metabolic network 900.

At 1102, process 1100 receives a metabolic network in a bipartite graph data structure. This may be the metabolic network 900 as described herein, which in some examples, is a graphical representation of the expanded bipartite metabolic network 100 as described in further detail with reference to FIG. 1. At 1202, process 1200 receives a metabolic network in a bipartite graph data structure. This may be the metabolic network 900 as described herein, which in some examples, is a graphical representation of the expanded bipartite metabolic network 100 as described in further detail with reference to FIG. 1.

The metabolic network 900 has input anchors 902 and output anchors 904. Input anchors 902 are shown in FIG. 9A-10C as bounded boxes, representing the anchored input nodes of the metabolic network 900. The input anchors 902 can be the input molecule nodes 102 as shown in FIG. 1, containing input anchor$_1$ 104, input anchor$_2$ 106, input anchor$_3$ 108, through input anchor$_N$ 110. Output anchors 904 are shown in FIG. 9A-10C as bounded boxes, representing the anchored output nodes of the metabolic network 900. The output anchors 904 can be the output molecule nodes 140 as shown in FIG. 1, containing output anchor$_1$ 142, output anchor$_2$ 144, output anchor$_3$ 146, through output anchor$_M$ 148. The input anchors 902 and output anchors 904 are not considered when identifying unused, unmade or intermediate nodes of the metabolic network 900. Following simplification of the metabolic network 900, specific anchors are shown at FIG. 10A for the remaining reaction pathways.

The metabolic network 900 contains a plurality of interconnected molecule nodes, such as molecule node 904, and a plurality of edges, such as edge 906. Metabolic network 900 is an un-simplified and un-condensed metabolic network, and thus may contain unmade nodes, unused nodes, and intermediate nodes. Metabolic network 900 may be assembled from primary literature, databases, biochemistry textbooks, conference presentations, or any other primary source literature.

XIV. Effect of Unused and Unmade Nodes on Metabolic Network

A pathway in a metabolic network is an ordered set of connected nodes and edges that are sequentially traversed from an input anchor to an output anchor. In a bipartite graph of a metabolic network, a pathway of the metabolic network is the ordered set of nodes and edges from an input anchor to an output anchor molecule node. A pathway of a metabolic network biologically represents the ordered series of chemical reactions that occur in converting an input anchor molecule to an output anchor molecule. If a pathway of a metabolic network includes an unused molecule node, then the pathway of the metabolic network consists of the ordered set of connected nodes and edges that are sequentially traversed from an input anchor to the unused molecule node. Thus a pathway with an unused molecule node does not fully traverse the metabolic network from input anchor to output anchor. If a pathway of a metabolic network includes an unmade molecule node, then the pathway of the metabolic network consist of the ordered set of connected nodes and edges that are sequentially traversed from the unmade molecule node to an output anchor. Thus a pathway with an unmade molecule node will not fully traverse the metabolic network form input anchor to output anchor. If a pathway contains both an unused molecule node and an unmade molecule node, the pathway of the metabolic network consists of the ordered set of connected nodes and edges sequentially traversed from the unmade molecule node to the unused molecule node. If a pathway of a metabolic network contains an orphan node, then the pathway may both begin and end with either an input anchor or an output anchor.

Because the un-simplified metabolic network 900 may contain molecule nodes that do not affect the flux value solutions of a mathematical simulation of the metabolic network 900, the computation associated with metabolic network 900 may contain more equations, constraints and variables than strictly necessary for solving for the flux value solutions of the input and output anchor molecules. For example, unused molecule nodes may result in entire reaction pathways with multiple molecule nodes and edges that all have zero flux at steady state of the metabolic network. The zero flux of the reaction pathway means that it does not affect the non-zero flux value solutions. However, during computation, each of the molecule nodes and edges may contribute variables, equations and constraints that are added to the overall computation, thus increasing the computation cost while ultimately not affecting the solutions at steady state. Thus it is possible, following analysis of the metabolic network 900 to reduce and condense the reaction pathways, to lower the computation burden for simulating the metabolic network 900. A process for identifying all of the unused, unmade and intermediate nodes, and reducing the metabolic network 900 accordingly, is described in further detail below.

A. Categorization

For each of the molecule nodes in the metabolic network 900, the number of metabolic reactions for which each molecule node is a product is determined by determining a number of edges into each molecule node. This may be at 1104 of process 1100, in which, for each molecule node of a bipartite graph data structure, a first number of metabolic reactions for which each molecule is a product is determined. For example, for each molecule node, a total number of edges leading into a molecule are counted. For each molecule node in the metabolic network 900, the number of metabolic reactions for which each molecule node is a reactant is determined by determining a number of edges out of each molecule node. This may correspond to 1106 of process 1100, in which, for each molecule node of a bipartite graph data structure, a first number of metabolic reactions for which each molecule is a product is determined. For example, for each molecule node, a total number of edges leading out of each molecule is counted.

Once the total number of edges leading into and out of each molecule node is determined, each molecule node can be categorized based on the categories defined in FIGS. 2-8. The category of each molecule node may be stored as metadata with the molecule node in the bipartite graph. If a molecule node is categorized as any of confluence 200, fork 300, nexus 400 or orphan 500, then the category of each molecule node is stored and no further action taken. If a molecule is categorized as any of an unused node 600, an unmade node 700 or an intermediate node 800, then the category of each molecule may still be stored, but the molecule node may be flagged for potential removal or blocking in the bipartite graph data structure.

As shown in FIG. 9A, following a first determination of the category of each molecule node, a total of six molecule nodes in the un-simplified metabolic network 900 are identified as unused or unmade nodes. Unused nodes 908, 910 and 912, as shown in FIG. 9, have edges leading into them, but zero edges leading out. Thus unused nodes 908, 910 and 912, while produced by a metabolic pathway, are not subsequently used as reactants in a chemical reaction, and may have zero flux at steady state of the metabolic network 900. Unmade nodes 914, 916 and 918, as shown in FIG. 9, have edges leading out of the molecule nodes, but zero edges leading into the molecule node. Thus unmade nodes 914, 916 and 918, while they could be used in downstream metabolic pathways, are not made within the metabolic network, and may have zero flux at steady state of the metabolic network 900.

Once categorized, the reaction pathways of unused nodes 908, 910 and 912, and unmade nodes 914, 916 and 918 are identified. A reaction pathway of an unused node, such as unused nodes 908, 910 and 912 consists of all nodes and edges connected to the unused node, as well as all connected nodes and edges upstream from the unused node, excluding connected input anchors. A reaction pathway of an unmade node, such as unmade nodes 914, 916 and 918 consists of all nodes and edges connected to the unmade node, as well as all connected nodes and edges downstream from the unmade node, excluding connected output anchors. The reaction pathways of unused and unmade nodes are described in further detail below.

B. Blocking Reaction Pathways

Figure 9B:
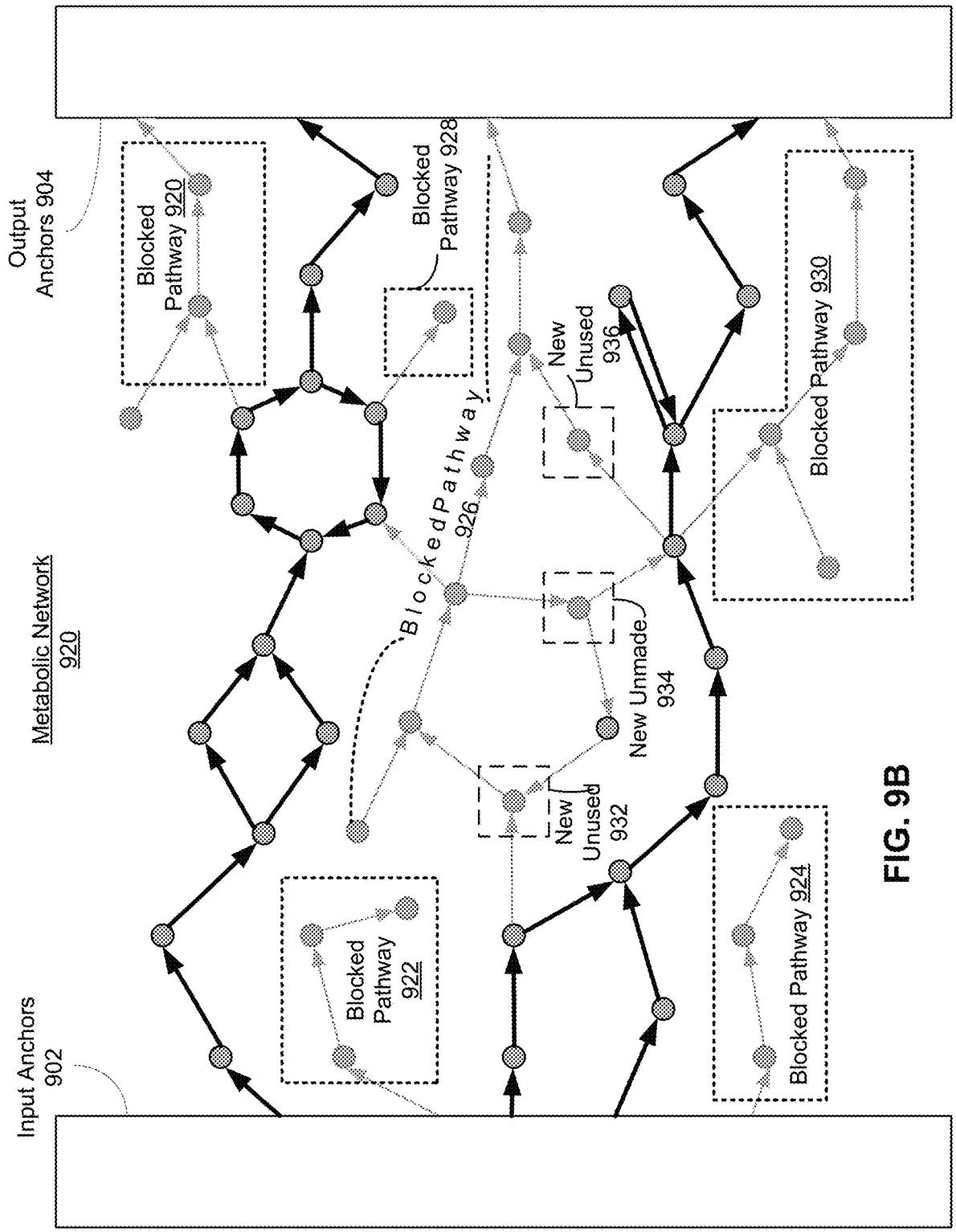
FIG. 9B is an abridged graphical representation of blocked pathways of the metabolic network of FIG. 9A, according to one embodiment.
Figure 10A:
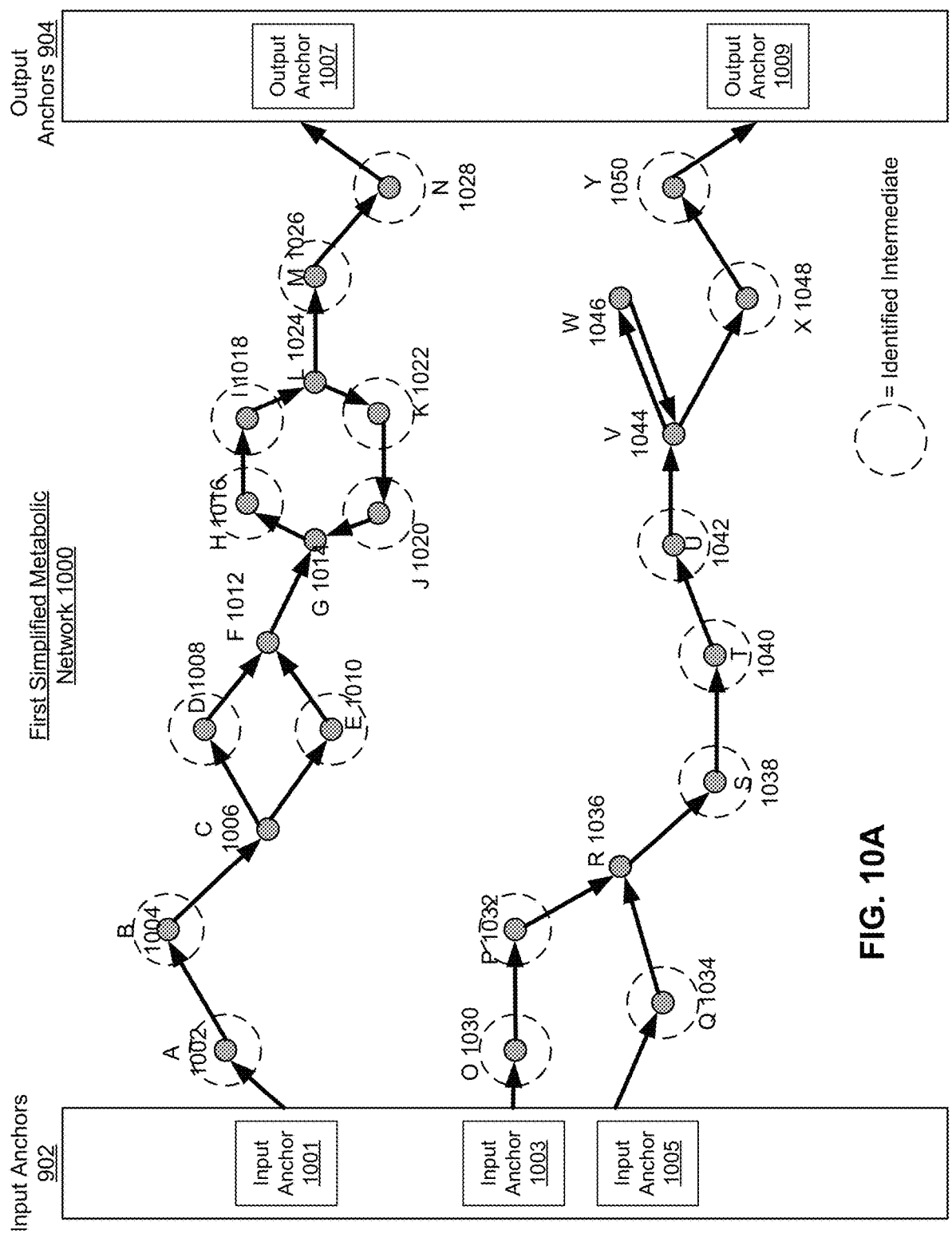
FIG. 10A is an abridged graphical representation of a first simplified metabolic network, according to one embodiment.

FIG. 9B is an abridged graphical representation of blocked pathways of the metabolic network 900 of FIG. 9A, according to one embodiment. FIG. 9B is described concurrently with the processes 1100 and 1200 of FIG. 11 and FIG. 12, respectively. Metabolic network 920 differs from the metabolic network 900 of FIG. 9A in that the reaction pathways of molecule nodes categorized as unused or unmade are blocked. Following a second iteration of categorization of each molecule node, new unused and unmade molecule nodes are identified as a result of the blocked reaction pathways.

Molecule nodes 908, 910, and 912 of metabolic network 900 are categorized as unused. As a result, in metabolic network 920, the reaction pathways of molecule nodes 908, 910 and 912 are blocked. This may correspond to 1108 of process 1100, in which, responsive to determining none of a first number of edges leads into a molecule node, or none of a second number of edges leads out of a molecule node, a first reaction pathway of all nodes and edges connected to the molecule node in the bipartite graph data structure is blocked. This may also correspond to 1204 of process 1200, in which each reaction pathway containing at least one unused or unmade molecule node is blocked. Reaction pathways of an unused node consist of all of the nodes and edges connected between the input anchors 902 and the unused node. The molecule nodes and edges are "upstream" of the unused node, meaning that in the bipartite graph, the connected set of nodes and edges terminate in an edge leading into the unused node. As shown in the graphical representations of metabolic networks 900 and 920, the "upstream" pathways are visually to the left of the unused nodes.

Blocking a reaction pathway of a metabolic network, such as in metabolic network 920, consists of taking the reaction pathway of the metabolic network out of mathematical simulations of the network. A blocked reaction pathway may be marked within the bipartite graph to identify it as a potential zero flux pathway. Specifically, a blocked reaction pathway will remain stored within the bipartite graph data structure, and thus still be "present" in the metabolic network, but will not be used in the mathematical simulations of the metabolic network. In some examples, blocking a reaction pathway consists of assigning zero flux values to one or more edges within the reaction pathway. Additionally or alternatively, blocking a reaction pathway consists of assigning zero concentration to one or more molecule nodes within the reaction pathway. In both of these examples, the zero flux values and/or zero concentration values may be added to the metadata of the edges and/or nodes of the bipartite graph. Any other method of mathematically eliminating the contribution of the nodes and edges to the computation of the mathematical simulation of the metabolic network may also be used.

As shown in FIG. 9B, following categorizing unused molecule node 910, a connected pathway is blocked at blocked pathway 924 to form metabolic network 920. Similarly, unused molecule node 908 leads to blocked pathway 922, and unused molecule node 912 leads to blocked pathway 928.

In a similar process, molecule nodes 914, 916, and 918 of metabolic network 900 are categorized as unmade. As a result, in metabolic network 920, the reaction pathways of molecule nodes 914, 916 and 918 are blocked. This may correspond to 1108 of process 1100, in which, responsive to determining none of a first number of edges leads into a molecule node, or none of a second number of edges leads out of a molecule node, a first reaction pathway of all nodes and edges connected to the molecule node in the bipartite graph data structure is blocked. This may also correspond to 1204 of process 1200, in which each reaction pathway containing at least one unused or unmade molecule node is blocked. Reaction pathways of an unmade node consist of all of the nodes and edges connected between the unmade node and the output anchors 904. The nodes and edges are "downstream" of the unmade node, meaning that in the bipartite graph, the connected set of downstream nodes and edges begin with an edge leading out of the unused node. As shown in the graphical representations of metabolic networks 900 and 920, the "downstream" pathways are visually to the right of the unused nodes.

As shown in FIG. 9B, following categorization of unmade node 914, a connected pathway is blocked at blocked pathway 926 to form metabolic network 920. Similarly, unmade node 916 leads to blocked pathway 920, and unmade node 918 leads to blocked pathway 930.

C. Checking Blocked Pathways

To determine if blocked pathways 920, 922, 924, 928 and 930 has no effect on the mathematical solutions to a simulation of the metabolic network, a check is run to determine if the identified blocked pathways do in fact have zero flux through the metabolic network 900. In some examples, an FBA simulation using the metabolic network 900 including all pathways is solved, and the set of flux value solutions for the pathways identified as blocked pathways is obtained. A first set of flux value solutions for the remaining metabolic pathways is also obtained. If the mathematical model for simulating metabolism is FBA, then the identified blocked pathways may have exactly 0 flux values. However, in cases where the mathematical model for simulating metabolism are based on ODEs, PDEs, Monte Carlo methods, or any other mathematical model that relies on numerical solutions to a set of equations, then the identified blocked pathways may not have exactly 0 flux values due to statistical and numerical approximations made within the model. However, flux values within a threshold of 0 are considered to have "zero-flux." Following obtaining a first set of flux values for the metabolic network that includes the identified blocked pathways, a second FBA simulation is run, this time using metabolic network 920 with the identified blocked pathways actually blocked in the metabolic network and the bipartite graph. A second set of flux value solutions for the remaining metabolic pathways is obtained. A comparison is made between the flux value solutions for the rest of the metabolic network before and after the identified blocked pathways are blocked from the metabolic network 900 to produce metabolic network 920.

If the flux value of the identified blocked pathways is zero when they are included in the mathematical simulations of the metabolic network, and after being blocked, the first set of flux value solutions for the remaining metabolic pathways is within a threshold value of the second set of flux value solutions, then the identified blocked pathways remain blocked in the metabolic network 920. If either of these conditions is not met, or the results are inconclusive, then the blocked pathway is unblocked or returned to the bipartite graph, and any identified unused and/or unmade molecule nodes and edges are included in future calculations of the metabolic model using the bipartite graph.

Figure 11:
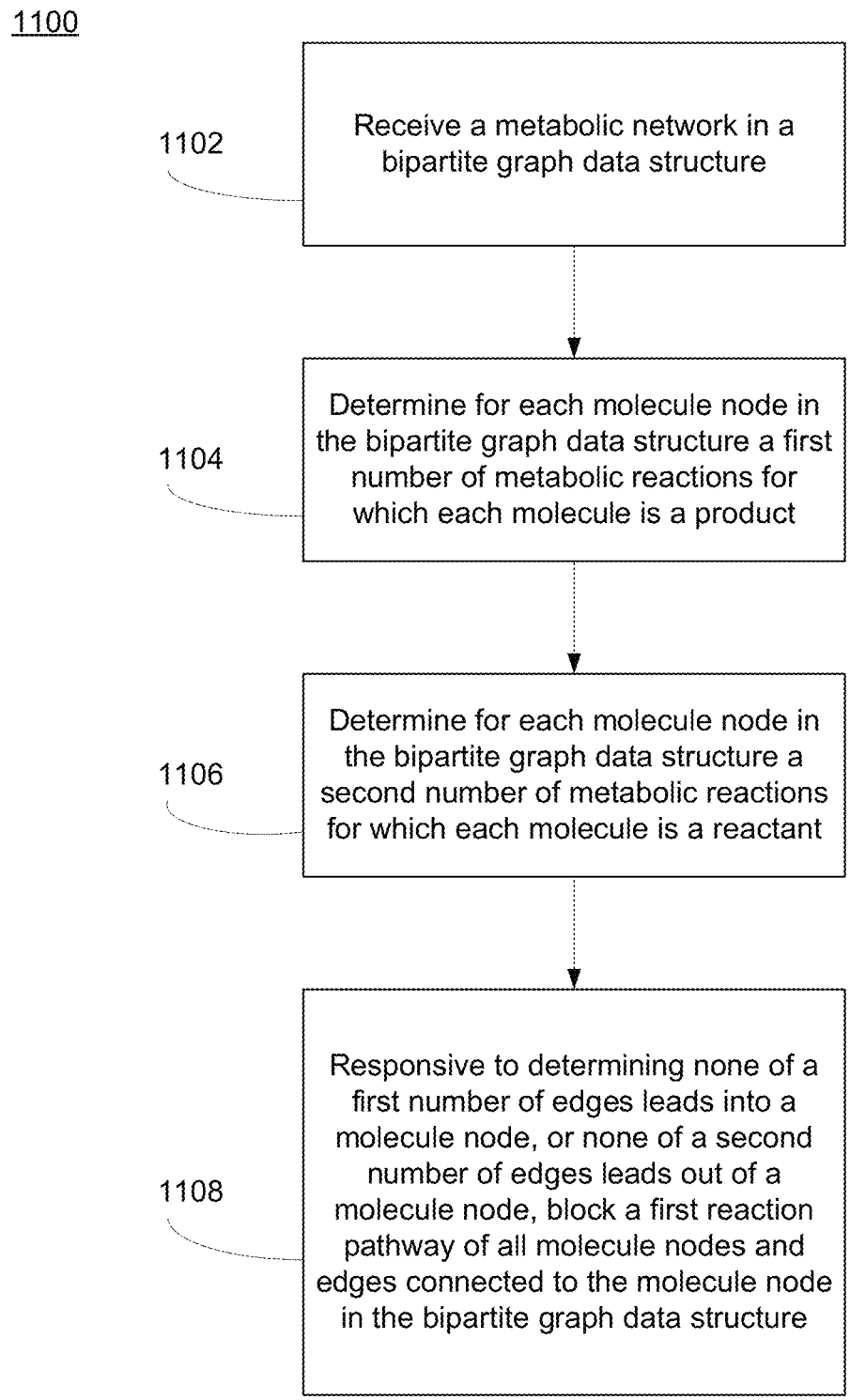
FIG. 11 shows a process for analyzing a bipartite graph data structure to condense reaction pathways of a metabolic network, according to one embodiment.

In some examples, an additional check is run to determine the effect of the unused and unmade nodes on the whole cell. An example of a metabolic network within a whole cell model is shown at FIG. 11. For example, a growth rate of the cell may be determined with the identified blocked pathways included in the mathematical simulation. Following blocking these pathways, a second growth rate of the cell may be determined. If the first growth rate is within a threshold value of the second growth rate, then the identified blocked pathways may remain blocked in the metabolic network 920. However, if the second growth rate is outside a threshold value of the first growth rate, then blocked pathways may be returned to the bipartite graph, such that the identified unused and/or unmade molecule notes and edges are included in future calculations of the metabolic model using the bipartite graph.

D. Multiple Iterations of Categorizing

Blocking pathways in the metabolic network may lead to the formation of new unused or unmade molecule nodes. For example, if a molecule node only has one edge leading out of it, and that edge is a part of a blocked pathway, then blocking the pathway will lead to the molecule node becoming an unused node. In the first categorization of molecule nodes, however, this molecule node would not have been categorized as unused. A similar process may occur with unmade nodes. Thus following an initial categorization and subsequent blocking of reaction pathways, subsequent categorization is needed to determine if any new unused or unmade nodes are created.

After blocking pathways 920, 922, 924 and 926, the molecule nodes of metabolic network 920 are once again categorized by counting the number of edges leading into and leading out of each molecule node. The categories are described in further detail with reference to FIG. 2-8. In some examples, this subsequent categorization identifies new unused or new unmade molecule nodes. For example, as shown in FIG. 9B, the blocked pathway 926 results in new unused molecule nodes 932 and 936, and a new unmade node 934. As described above, the reaction pathways for these new unused and unmade nodes are then identified as potential blocked pathways, checked, and may remain removed from the metabolic network or be returned to the metabolic network. Returning a blocked pathway to the bipartite graph means that all previously blocked nodes and edges are unblocked, such that they are included within the bipartite graph structure and future calculations of the metabolic model using the bipartite graph. This process may continue until no new unused or unmade molecule nodes are identified within the metabolic network. This may correspond to 1108 of process 1100, in which, responsive to determining none of a first number of edges leads into a molecule node, or none of a second number of edges leads out of a molecule node, a first reaction pathway of all molecule nodes and edges connected to the molecule node in the bipartite graph data structure is blocked. This may also correspond to 1204 of process 1200, in which each reaction pathway containing at least one unused or unmade molecule node is blocked.

The process of blocking reaction pathways of unused and unmade molecule nodes thus may potentially reduce the number of nodes and edges in the bipartite graph. By blocking these reaction pathways, the computation associated with simulating the metabolic network 900 can be reduced to the reaction pathways that affect the flux value solutions of metabolic network 900. Assuming that the blocked pathways, and the new unused and new unmade molecule nodes as shown in FIG. 9B all are determined to have zero flux and blocking them from the metabolic network 900 does not change the flux value solutions outside of a threshold boundary, then they may remain blocked in the metabolic network 920. The subsequent metabolic network is shown and discussed in further detail with reference to FIG. 10A-10C.

XV. Removing Intermediate Nodes

Figure 10B:
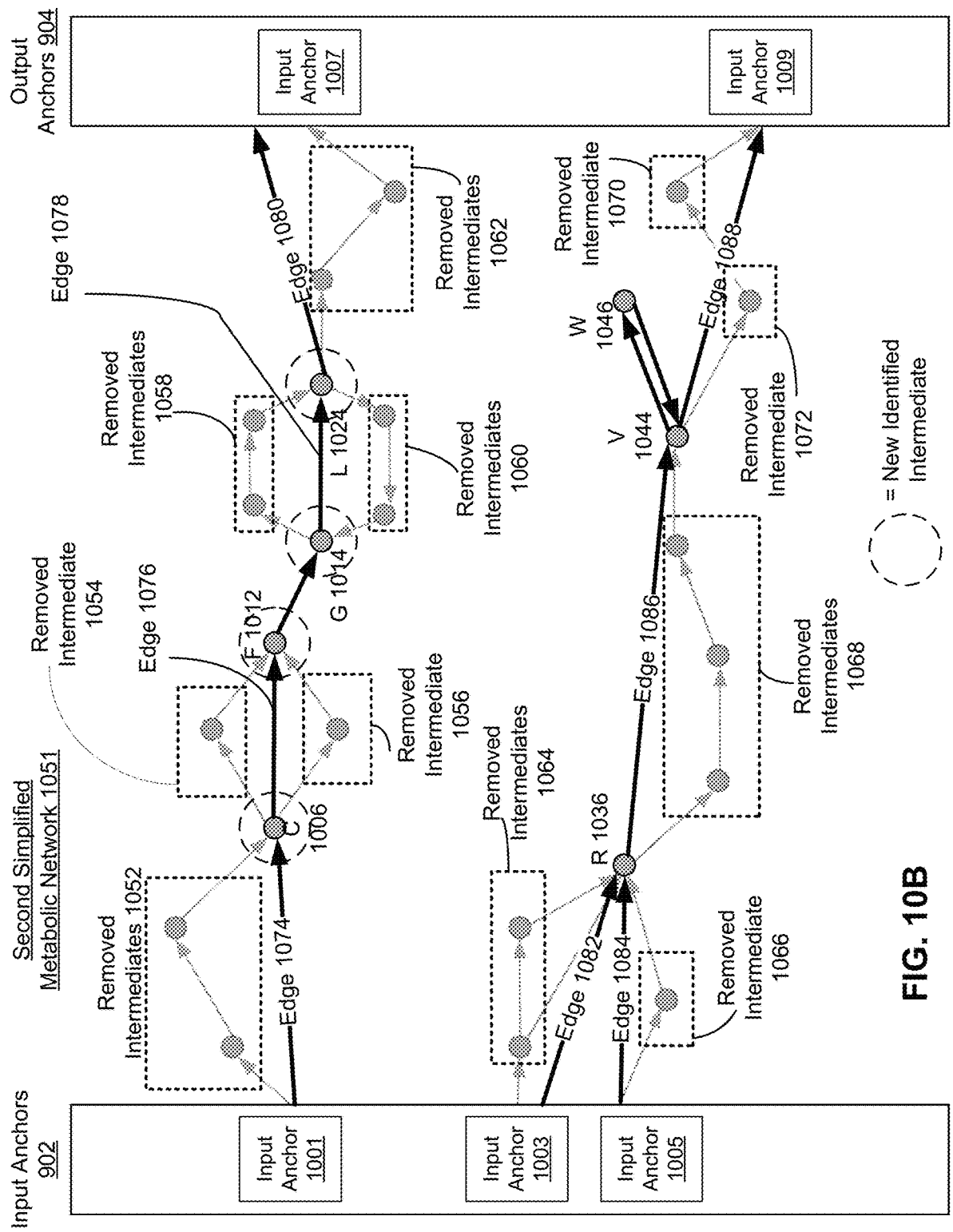
FIG. 10B is an abridged graphical representation of removed pathways of the first simplified metabolic network of FIG. 10A, according to one embodiment.

FIG. 10A is an abridged graphical representation of a first simplified metabolic network 1000, according to one embodiment. FIGS. 10A-10B are described below concurrently with process 1200 of FIG. 12. The first simplified metabolic network 1000 is the metabolic network 900 as shown in FIG. 9A following the blocking of reaction pathways of all unused and unmade molecule nodes. As shown in FIG. 10A, the blocked pathways have been visually eliminated from the metabolic network 920, but may remain as blocked pathways within a bipartite graph. Additionally, the input anchors 1001, 1003, 1005 of the remaining metabolic pathways are shown within the input anchors 902. The output anchors 1007 and 1009 of the remaining metabolic pathways are also shown within the output anchors 904. The first simplified metabolic network 1000 may represent a significant reduction in computation from the original, unsimplified metabolic network 900. However, further simplification of the first simplified metabolic network 1000 is possible by removal of intermediate molecule nodes and subsequent condensing of metabolic pathways. This process is described in further detail below, and may correspond to 1206 of process 1200, in which each reaction pathway containing at least one intermediate molecule node is condensed. As previously described in relation to FIG. 8, intermediate molecule nodes do not contribute to the flux balance solutions of a metabolic network, beyond defining the reaction pathway between the input anchors 902 and output anchors 904. Intermediate molecule nodes can be removed by replacing them with new edges linking the molecule nodes directly adjacent to the intermediate node through a remaining process node, thus preserving the reaction pathway while condensing the intermediate node and its two connected edges.

Thus as described herein, removal of a pathway or node from a bipartite graph consists of "short-circuiting" the pathway or node by forming new edges between the adjacent molecule nodes in the bipartite graph. Thus the bipartite graph is re-structured such that the intermediate node and/or pathway is not traversed by the remaining reaction pathway between input anchors and output anchors.

For example, first the intermediate nodes of a simplified metabolic network are identified and categorized by analyzing the structure of the bipartite graph. Thus, for each molecule node in the first simplified metabolic network 100, the number of input edges and output edges is determined, and each node categorized according to the categories described in FIG. 2-8. As shown in first simplified metabolic network 100, the molecule nodes A 1002, B 1004, D 1008, E 1010, H 1016, I 1018, J 1020, K 1022, M 1026 and N 1028 of the upper reaction pathway are all identified as intermediate nodes because each of these molecule nodes has a single edge leading into the node and a single edge leading out of the molecule node. The upper reaction pathway then constitutes the input anchor 1001, molecule node C 1006, molecule node F 1012, molecule node G 1014, molecule node L 1024 and output anchor 1007. The molecule nodes O 1030, P 1032, S 1038, T 1040, U 1042, X 1048 and Y 1050 are also identified as intermediate nodes of the bottom reaction pathway in the bottom reaction pathway. To bottom reaction pathway then constitutes the input anchor 1003, input anchor 1005, molecule node R 1036, molecule node V 1044, molecule node W 1046 and output anchor 1009.

XVI. Forming New Edges

FIG. 10B is an abridged graphical representation of removed intermediate nodes of the first simplified metabolic network 1000 of FIG. 10A, according to one embodiment. The result is the second simplified metabolic network 1051. The removed intermediates as shown in FIG. 10B are portions of the reaction pathways with intermediate molecule nodes, as categorized in FIG. 10A. For each removed intermediate molecule node and its adjacent edges, edges are drawn linking the immediately adjacent molecule nodes, and any remaining process nodes. Before removing intermediate molecule nodes, the same check procedures as described with relation to FIGS. 9A-9B may confirm that removal of intermediate molecule nodes does not affect the flux value solutions to the metabolic network. This process may correspond to 1206 of process 1200, in which each reaction pathway containing at least one intermediate molecule node is condensed.

Figure 10C:
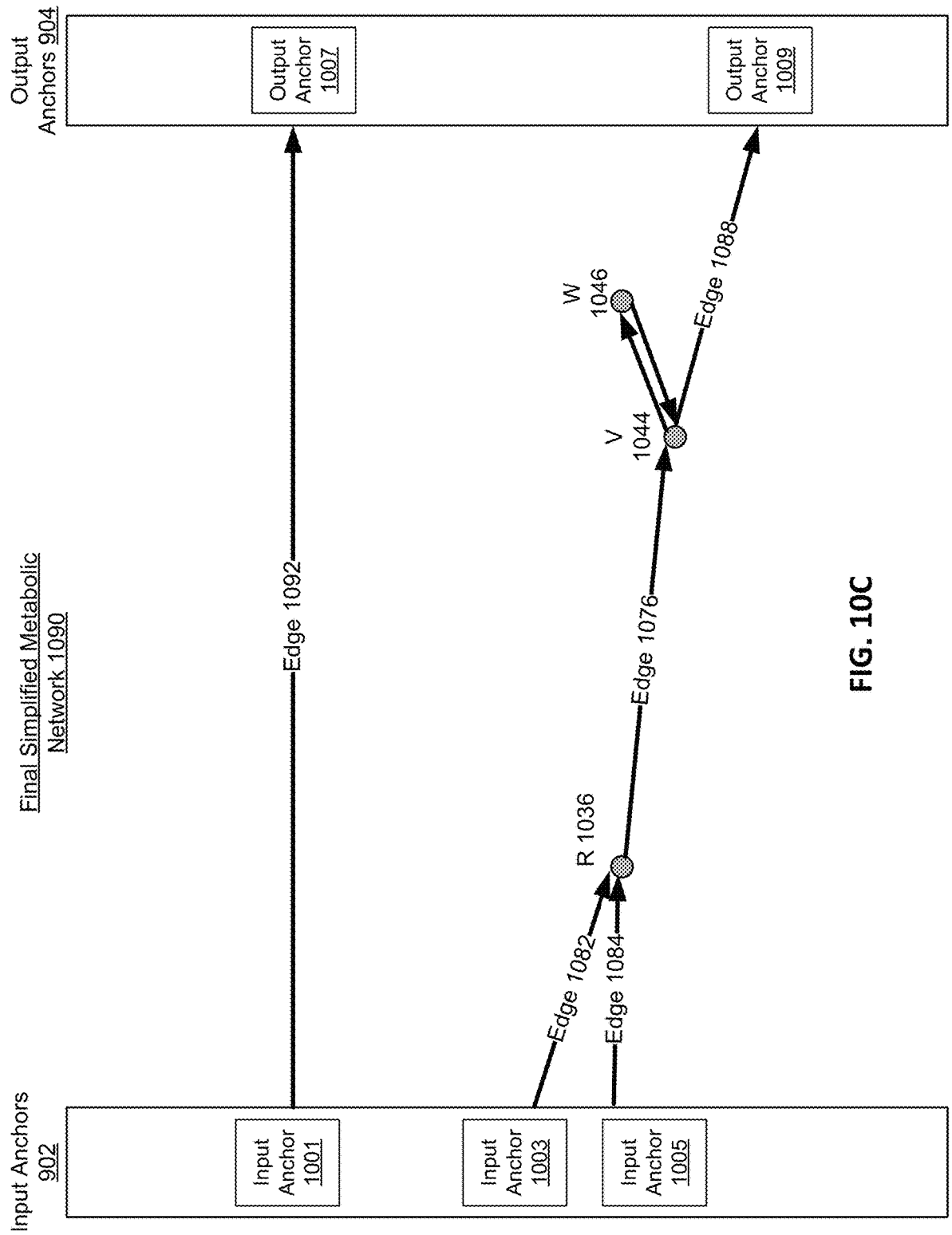
FIG. 10C is an abridged graphical representation of a final simplified metabolic network, according to one embodiment.

For example, as shown in FIG. 10A, molecule nodes A 1002 and B 1004 are categorized as an intermediate nodes. Molecule nodes A 1002 and B 1004 and their adjacent edges are removed from the metabolic network as shown at removed intermediates 1052. A new edge 1074 is created between the input anchor 1001 and molecule node C 1006, which intermediate nodes A 1002 and B 1004 had previously connected. Thus edge 1074 replaces the removed intermediates 1052 while maintaining the reaction pathway between the input anchor 1001 and molecule node C 1006, which remain in the upper reaction pathway. Within the bipartite graph, removing intermediate nodes entails removing the molecule nodes categorized as intermediates, and the edges leading into the intermediate nodes, the edge leading out of the intermediate nodes. Between the adjacent remaining molecule nodes, new edges are formed that effectively short circuits the intermediate path, such as edge 1074 as shown in FIG. 10B. While, as shown in FIGS. 10B and 10C, new edges are single edges, it should be understood that within the bipartite data structure, any number of edges may be formed between remaining molecule nodes to process nodes that maintain the structure of the reaction pathway. For example, edge 1074 between input anchor 1001 and molecule node C 1006 may be any number of edges that link input anchor 1001 and molecule node C 1006 to any of the process nodes previously connected to the removed intermediates 1052.

Similarly, molecule node D 1008 and its adjacent edges are removed from the bipartite graph at removed intermediate 1054. Molecule node E 1010 and its adjacent edges are removed from the bipartite graph at removed intermediate 1056. Edge 1076 replaces both removed intermediate 1054 and removed intermediate 1056. Molecule nodes H 1016 and I 1018 are both removed from the bipartite graph at removed intermediates 1058. Molecule nodes J 1020 and K 1022 are also both removed at removed intermediates 1060. Edge 1078 replaces both removed intermediate 1058 and removed intermediate 1060. Molecule nodes M 1026 and N 1028 are removed at removed intermediates 1062. Edge 1080 replaces the removed intermediates 1062.

In the bottom reaction pathway, molecule nodes O 1030 and P 1032 are removed from the bipartite graph at removed intermediates 1064. Edge 1082 replaces the removed intermediates 1064. The molecule node Q 1034 is removed at removed intermediate 1066 and replaced with edge 1084. The molecule nodes S 1038, T 1040, and U 1042 are removed at removed intermediates 1068. Edge 1086 replaces the removed intermediates 1068. The molecule node X 1048 is removed at removed intermediate 1072. The molecule node Y 1050 is removed at removed intermediate 1070. Edge 1088 replaces the removed intermediate 1072 and removed intermediate 1070.

A. Iterating Categorization of Intermediates

Following removing the molecule nodes categorized as intermediates at FIG. 10A, new intermediates may be formed. For example, following a second iteration of categorizing the remaining molecule nodes, new intermediate molecule nodes C 1006, F 1012, G 1014 and L 1024 are identified and categorized. These new intermediates may then be removed and replaced by new edges, as is shown below with reference to FIG. 10C. The remaining molecule nodes may be categorized and any identified intermediate nodes removed until no new intermediate nodes are found. For example, as shown in FIG. 10B, following the removal of new intermediate nodes C 1006, F 1012, G 1014 and L 1024, no new intermediate nodes are formed within the metabolic network. This process may correspond to 1206 of process 1200, in which each reaction pathway containing at least one intermediate molecule node is condensed.

B. New Edges

In addition to the links between any process nodes previously connected to removed intermediate molecule nodes, the newly formed edges, which in FIG. 10B are shown as edge 1074, edge 1076, edge 1078, edge 1080, edge 1078, edge 1082, edge 1084, edge 1086 and edge 1088, retain and store the metadata of the removed intermediates that they replace. Thus, for example, edge 1086 may store all or some of the metadata stored at molecule nodes S 1038, T 1040, U 1042 and each of their adjacent edges. The metadata information stored in edge 1086 may retain the metadata information regarding the stoichiometry of the chemical reaction between molecule node S 1038 and molecule node T 1040, as well as the molecular formula of molecule nodes S 1038 and T 1040. Retaining metadata of removed intermediates in newly formed edges allows the metabolic pathway to reduce the number of nodes and edges stored in the bipartite graph data structure, and the computation associated with any mathematical simulation using the bipartite graph, without loss of information for potentially influencing the metabolic pathway. For example, molecule node B 1004 may be removed from the upper metabolic pathway as shown in FIG. 10B, but molecule node B 1004 may be retained as a potential target for interrupting or affecting the metabolic pathway between input anchor 1001 and output anchor 1007 by storing it in edge 1074.

The new identified intermediate molecule nodes, molecule node C 1006, molecule node F 1012, molecule node G 1014, and molecule node L 1024 are similarly removed from the metabolic pathway and replaced with new edges that may retain metadata of the removed intermediate pathways. This process may correspond to 1206 of process 1200, in which each reaction pathway containing at least one intermediate molecule node is condensed. The result is shown at FIG. 10C.

XVII. Final Simplified Metabolic Network

FIG. 10C is an abridged graphical representation of a final simplified metabolic network 1090, according to one embodiment. The new identified intermediate molecule nodes shown in FIG. 10B are removed and replaced with edge 1092, which connects the input anchor 1001 and the output anchor 1007. As shown in FIG. 10C, the final simplified metabolic network 1084 consists of anchor molecule nodes and molecule nodes categorized as one of a confluence node, fork node, nexus node or orphan node, as described with reference to FIG. 2-5. Thus the upper metabolic reaction pathway between input anchor 1001 and output anchor 10076 shown in the first simplified metabolic network 1000 as consisting of fourteen molecule nodes and 17 connected edges is simplified to a single edge 1092. The lower reaction pathway connecting input anchors 1003 and 1005 and the output anchor 1009 is simplified to three molecule nodes and six edges, from the eleven molecule nodes and fourteen edges as shown in the first simplified metabolic network 1000.

Using the final simplified metabolic network 1090, the flux value solutions for each of the anchor molecules, input anchor 1001, input anchor 1003, input anchor 1005, output anchor 1007 and output anchor 1009 can be solved for using a mathematical simulation with steady state assumptions, such as an FBA model of metabolism.

Comparing the final simplified metabolic network 1090 with the original metabolic network 900 as shown in FIG. 9A, the process of blocking zero flux pathways, as well as condensing remaining reaction pathways by removing intermediate molecule nodes results in a significant reduction in the number of molecule nodes and edges in the bipartite graph. This translates to a reduction in the computation associated with using these bipartite graphs to perform mathematical simulations of the metabolic network 900. The metabolic networks as shown in FIG. 9A-10C may be several orders of magnitude smaller than a true representation of all of the molecule nodes and edges for a cell's metabolic network, and are described herein as an example of the reduction in complexity that results from analyzing the structure of a bipartite graph. Scaling the benefits of the reduction in the bipartite graph shown from FIG. 9A to FIG. 10C up several orders of magnitude, however, may result in a 50 percent reduction in the size of the bipartite graph of a metabolic network.

XVIII. Metabolic Network in Full Cell Model

Figure 13:
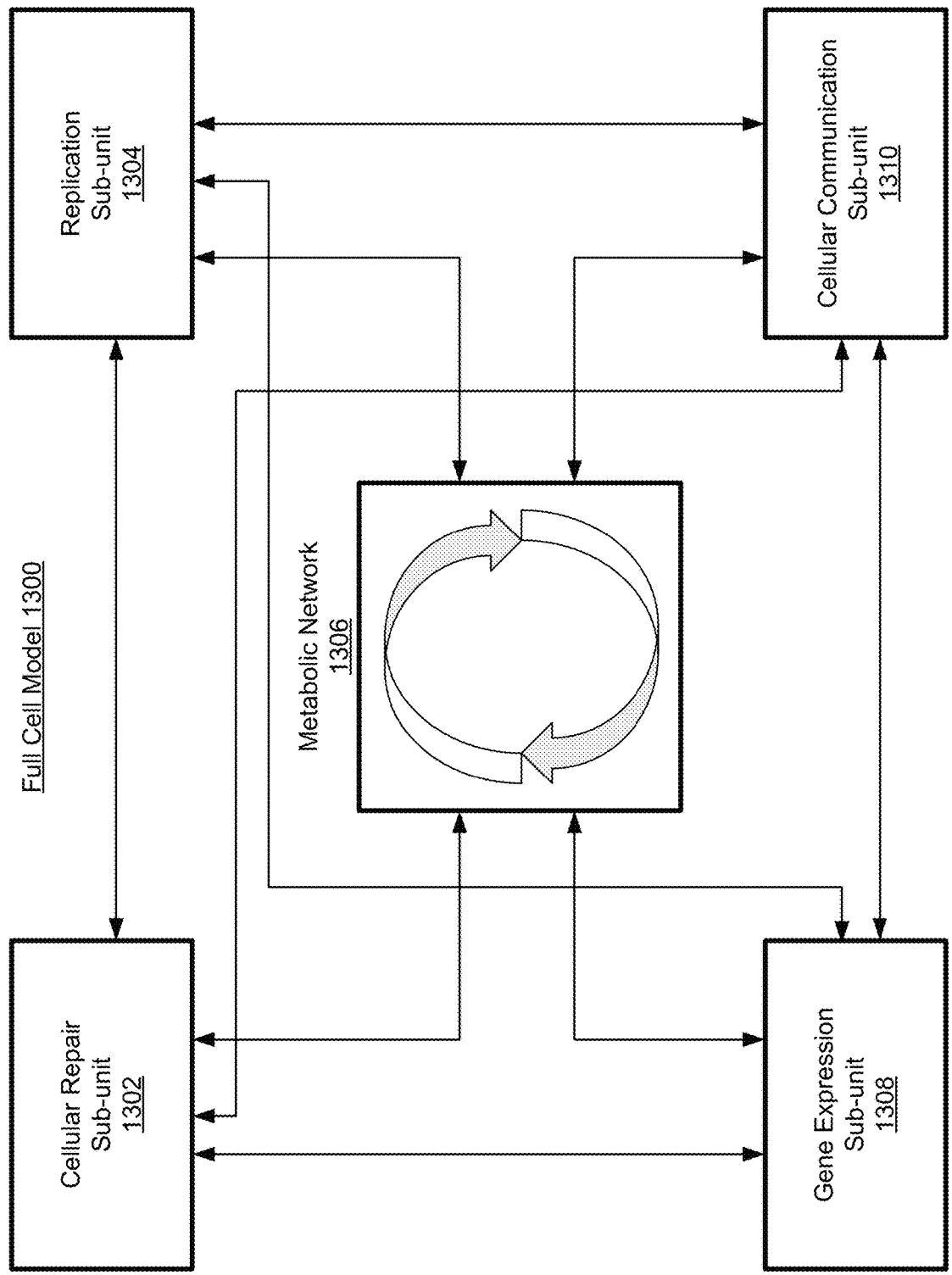
FIG. 13 is a block diagram of a metabolic network in the context of a full cell model, according to one embodiment.

FIG. 13 is a block diagram of a metabolic network in the context of a full cell model 1300, according to one embodiment. Following the simplification of a bipartite graph metabolic network, the network can be incorporated into a full cell model, in which the input molecule nodes 102 and input anchors 902 interface with upstream cellular processes external to metabolism. For example, the input molecule nodes 102 and input anchors 902 may originate from any of the cellular processes sub-units shown in the full cell model 1300, such as cellular repair sub-unit 1302, replication sub-unit 1304, gene expression sub-unit 1308 and/or cellular communication sub-unit 1310. Similarly, the output molecule nodes 140 and output anchors 904 interface with the downstream cellular processes, such that the products of the metabolic molecule are inputs to cellular repair sub-unit 1302, replication sub-unit 1304, gene expression sub-unit 1308, and/or cellular communication sub-unit 1310. The input flux values associated with the input molecule nodes 102 and input anchors may thus represent the rate at which the metabolic network 1306 takes in molecules from these cellular processes. The output flux values associated with the output molecule nodes 140 and output anchors 904 similarly may represent the rate at which these cellular processes take in the products of metabolism to their own chemical reactions.

Before blocking a molecule node categorized as unused or unmade, a growth rate of the full cell model 1300 may be determined. A growth rate of the full cell model 1300 may be represented by the rate of change of biomass across all of the cellular processes within the full cell model 1300. Thus prior to blocking an unused or unmade molecule node from the bipartite graph, a simulation of the full cell model 1300 may be run, and a growth rate determined. The unused or unmade molecule node and its reaction pathway may then be blocked within the bipartite graph. A second growth rate is determined by running a simulation of the full cell model 1300 with these nodes and pathways blocked. If the first growth rate of the full cell model 1300 is within a threshold of the second growth rate, then the unused or unmade molecule nodes remain blocked in the bipartite graph. If the growth rate is outside of a threshold value, then the blocked pathway and molecule nodes are returned to the bipartite graph such that these nodes and pathways are no longer blocked, and are included in future calculations of the metabolic model. When comparing a first growth rate of the full cell model 1300 to a second growth rate of the cell model with blocked pathways and molecule nodes, a number of simulations are run. For example, 100 simulations may be run of both the full cell model 1300 and a model with blocked pathways and molecule nodes. A mean and variance of the resulting distributions may be compared. If the mean and variance are the same or within a threshold value of each other before and after blocking pathways, the pathways may remain blocked. If the mean and variance are not the same or differ by greater than a threshold value, the blocked pathways may be un-blocked and returned to the bipartite graph.

A number of embodiments have been described. Nevertheless, it will be understood that various modifications may be made without departing from the spirit and scope of the invention.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims

What is claimed is:

1. A method for analyzing a bipartite graph data structure to condense reaction pathways of a metabolic network, comprising:

receiving a metabolic network in a bipartite graph data structure, comprising:
   a plurality of molecule nodes, wherein each molecule node comprises a molecule in a metabolic reaction; and
   a plurality of edges connecting at least two of the plurality of molecule nodes, wherein each edge leading out of a first molecule node and into a second molecule node represents a metabolic reaction in which the first molecule is a reactant and the second molecule is a product;
determining for each molecule node in the bipartite graph data structure a first number of metabolic reactions for which each molecule is a product based on a first number of edges leading into each molecule node;
determining for each molecule node in the bipartite graph data structure a second number of metabolic reactions for which each molecule is a reactant based on a second number of edges leading out of each molecule node;
responsive to determining that none of the first number of edges leads into a third molecule node, or none of the second number of edges leads out of the third molecule node, blocking a first reaction pathway of all molecule nodes and edges connected to the third molecule node in the bipartite graph data structure; and
receiving a growth rate of a cell model using the bipartite graph data structure in a mathematical simulation of the metabolic network.

2. The method of claim 1, further comprising:
responsive to blocking a first reaction pathway of all molecule nodes and edges connected to the third molecule node in the bipartite graph data structure:
   receiving a first flux value in the first reaction pathway at a steady state of the metabolic network; and
   blocking the first reaction pathway from the bipartite graph data structure if the first flux value is below a threshold flux through the first reaction pathway at the steady state.

3. The method of claim 2, further comprising:
receiving a second flux value of a second reaction pathway at the steady state of the metabolic network;
receiving a third flux value of the second reaction pathway at the steady state of the metabolic network; and
responsive to determining that the third flux value is outside of a threshold of the second flux value, returning the first reaction pathway to the bipartite graph data structure.

4. The method of claim 2, further comprising:
responsive to blocking the first reaction pathway from the bipartite graph data structure, storing the first reaction pathway in a supplementary bipartite graph data structure.

5. The method of claim 1, further comprising:
responsive to determining that the first number of edges leading into the second molecule node is one, and the second number of edges leading out of the second molecule node is one, removing the second molecule node from the bipartite graph data structure.

6. The method of claim 5, further comprising:
responsive to removing the second molecule node from the bipartite graph data structure, replacing the first molecule node and a fourth molecule node connected to the second molecule node with at least one new edge.

7. The method of claim 6, further comprising:
storing information for the second molecule node within the at least one new edge between the first molecule node and the fourth molecule node.

8. The method of claim 1, further comprising:
classifying each molecule node in the bipartite graph data structure as one of: a confluence node, a nexus node, a fork node, an orphan node, an unused node, an unmade node, or an intermediate node.

9. The method of claim 1, further comprising:
determining the first number of edges leading into each molecule node and the second number of edges leading out of each molecule node until all molecule nodes in the bipartite graph data structure contain a sum total of at least three connected edges, is an orphan node, or receiving a flux value indicating zero flux through a reaction pathway at a steady state of the metabolic network.

10. The method of claim 1, wherein the mathematical simulation of the metabolic network is based at least in part on a flux balance analysis (FBA) model.

11. A non-transitory computer readable storage medium containing computer program code executable on a processor for analyzing a bipartite graph data structure to condense reaction pathways of a metabolic network, the computer program code for:
receiving a metabolic network in a bipartite graph data structure, comprising:
   a plurality of molecule nodes, wherein each molecule node comprises a molecule in a metabolic reaction;
   a plurality of edges connecting at least two of the plurality of molecule nodes, wherein each edge leading out of a first molecule node and into a second molecule node represents a metabolic reaction in which the first molecule is a reactant and the second molecule is a product;
   determining for each molecule node in the bipartite graph data structure a first number of metabolic reactions for which each molecule is a product based on a first number of edges leading into each molecule node;
   determining for each molecule node in the bipartite graph data structure a second number of metabolic reactions for which each molecule is a reactant based on a second number of edges leading out of each molecule node;
   responsive to determining that none of the first number of edges leads into a third molecule node, or none of the second number of edges leads out of the third molecule node, blocking a first reaction pathway of all molecule nodes and edges connected to the third molecule node in the bipartite graph data structure; and
   receiving a growth rate of a cell model using the bipartite graph data structure in a mathematical simulation of the metabolic network.

12. The computer-readable medium of claim 11, the computer program code further for:
determining the first number of edges leading into each molecule node and the second number of edges leading out of each molecule node until all molecule nodes in the bipartite graph data structure contain a sum total of at least three connected edges or receiving a flux value indicating movement through a reaction pathway at a steady state of the metabolic network.

13. The computer-readable medium of claim 11, wherein the mathematical simulation of the metabolic network is based at least in part on a flux balance analysis (FBA) model.

14. A system comprising:
one or more data processors; and
a non-transitory computer readable storage medium containing instructions which, when executed on the one or more data processors, cause the one or more data processors to perform a set of actions comprising:
   receiving a metabolic network in a bipartite graph data structure, comprising:
      a plurality of molecule nodes, wherein each molecule node comprises a molecule in a metabolic reaction;
      a plurality of edges connecting at least two of the plurality of molecule nodes, wherein each edge leading out of a first molecule node and into a second molecule node represents a metabolic reaction in which the first molecule is a reactant and the second molecule is a product;
   determining for each molecule node in the bipartite graph data structure a first number of metabolic reactions for which each molecule is a product based on a first number of edges leading into each molecule node;
   determining for each molecule node in the bipartite graph data structure a second number of metabolic reactions for which each molecule is a reactant based on a second number of edges leading out of each molecule node;
   responsive to determining that none of the first number of edges leads into a third molecule node, or none of the second number of edges leads out of the third molecule node, blocking a first reaction pathway of all molecule nodes and edges connected to the third molecule node in the bipartite graph data structure; and
   receiving a growth rate of a cell model using the bipartite graph data structure in a mathematical simulation of the metabolic network.

15. The system of claim 14, wherein the set of actions further includes:
   responsive to blocking a first reaction pathway of all molecule nodes and edges connected to the third molecule node in the bipartite graph data structure:
      receiving a first flux value in the first reaction pathway at a steady state of the metabolic network; and
      blocking the first reaction pathway from the bipartite graph data structure if the first flux value is below a threshold flux through the first reaction pathway at the steady state.

16. The system of claim 15, wherein the set of actions further includes:
   receiving a second flux value of a second reaction pathway at the steady state of the metabolic network;
   receiving a third flux value of the second reaction pathway at the steady state of the metabolic network; and
   responsive to determining that the third flux value is outside of a threshold of the second flux value, returning the first reaction pathway to the bipartite graph data structure.

17. The system of claim 15, wherein the set of actions further includes:
   responsive to blocking the first reaction pathway from the bipartite graph data structure, storing the first reaction pathway in a supplementary bipartite graph data structure.

18. The system of claim 15, wherein the set of actions further includes:
   responsive to determining that the first number of edges leading into the second molecule node is one, and the second number of edges leading out of the second molecule node is one, removing the second molecule node from the bipartite graph data structure.

19. The system of claim 18, wherein the set of actions further includes:
   responsive to removing the second molecule node from the bipartite graph data structure, replacing the first molecule node and a fourth molecule node connected to the second molecule node with at least one new edge.

20. The system of claim 19, wherein the set of actions further includes:
   storing information for the second molecule node within the at least one new edge between the first molecule node and the fourth molecule node.

* * * * *